(12) United States Patent
Ye et al.

(10) Patent No.: US 10,202,611 B2
(45) Date of Patent: *Feb. 12, 2019

(54) VECTORS AND METHODS FOR IMPROVED PLANT TRANSFORMATION EFFICIENCY

(71) Applicant: MONSANTO TECHNOLOGY LLC, St. Louis, MO (US)

(72) Inventors: Xudong Ye, Chesterfield, MO (US); Larry A. Gilbertson, Chesterfield, MO (US); Michael W. Petersen, Sauk City, WI (US)

(73) Assignee: Monsanto Technology LLC, St. Louis, MO (US)

( * ) Notice: Subject to any disclaimer, the term of this patent is extended or adjusted under 35 U.S.C. 154(b) by 837 days.

This patent is subject to a terminal disclaimer.

(21) Appl. No.: 14/642,674

(22) Filed: Mar. 9, 2015

(65) Prior Publication Data

US 2015/0232865 A1    Aug. 20, 2015

Related U.S. Application Data

(62) Division of application No. 11/516,036, filed on Sep. 5, 2006, now Pat. No. 8,993,846.

(60) Provisional application No. 60/714,501, filed on Sep. 6, 2005.

(51) Int. Cl.
*C12N 15/84* (2006.01)
*C12N 15/82* (2006.01)

(52) U.S. Cl.
CPC .................. *C12N 15/8205* (2013.01)

(58) Field of Classification Search
None
See application file for complete search history.

(56) References Cited

U.S. PATENT DOCUMENTS

| | | |
|---|---|---|
| 5,004,863 A | 4/1991 | Umbeck |
| 5,034,322 A | 7/1991 | Rogers et al. |
| 5,159,135 A | 10/1992 | Umbeck |
| 5,518,908 A | 5/1996 | Corbin et al. |
| 5,550,038 A | 8/1996 | Goodman et al. |
| 5,591,616 A | 1/1997 | Hiei et al. |
| 5,750,871 A | 5/1998 | Moloney et al. |
| 5,824,877 A | 10/1998 | Hinchee et al. |
| 5,846,797 A | 12/1998 | Strickland |
| 6,117,677 A * | 9/2000 | Thompson ............... A23D 9/00 435/183 |
| 6,384,301 B1 | 5/2002 | Martinell et al. |
| 6,624,344 B1 | 9/2003 | Rangan et al. |
| 6,696,621 B2 | 2/2004 | Kloti et al. |
| 7,002,058 B2 | 2/2006 | Martinell et al. |
| 7,402,734 B2 | 7/2008 | Martinell et al. |
| 2004/0172681 A1 * | 9/2004 | Voelker ................ C12N 9/1029 800/281 |

FOREIGN PATENT DOCUMENTS

| | | |
|---|---|---|
| WO | WO 2002/068598 | 2/2002 |
| WO | WO 2004/092390 | 9/2004 |

OTHER PUBLICATIONS

U.S. Appl. No. 14/298,739, filed Feb. 5, 2015, Ye et al.
Ammirato et al., "Yams," In: Handbook of *Plant Cell Culture* —Crop Species, Macmillan Publ. Co., vol. 3, pp. 327-354,New York, 1984.
Bevan, "Binary agrobacterium vectors for plant transformation," *Nucleic Acids Research*, 12(22):8711-8721, 1984.
Binns et al., "The genetic and chemical basis of recognition in the *Agrobacterium*:plant interaction," In: *Bacterial Pathogenesis of Plants and Animals, Molecular and Cellular Mechanisms*, Dangl (Ed.), Stringer Verlag, Berlin, Germany, pp. 119-138, 1994.
Broothaerts et al., "Gene transfer to plants by diverse species of bacteria," *Nature*, 433:629-633, 2005.
Cevallos et al, "*Rhizobium etli* CFN42 contains at least three plasmids of the repABC family: a structural and evolutionary analysis," *Plasmid*, 48:104-116, 2002.
Datta et al., "Genetically engineered fertile indica-rice recovered from protoplasts ," *Bio/Technology*, 8:736-740, 1990.
Fraley et al., "The SEV system: a new disarmed Ti Plasmid vector system for plant transformation," *Bio/Technology*, 3:629-635, 1985.
Gelvin, "Molecular genetics of T-DNA transfer from *Agrobacterium* to plants," In: *Transgenic Plants*, Kung et al. (eds.), Academic Press, San Diego, vol. 1, pp. 49-87, 1993.
Grevelding et al., Single copy T-DNA insertions in *Arabidopsis* are the predominant form of integration in root-derived transgenics, whereas multiple insertions are found in leaf discs. *Plant Mol. Biol.* Nov: 23(4): 847-60: 1993.
Hayashimoto et al., "A polyethylene glycol-mediated protoplast transformation system for production of fertile transgenic rice plants," *Plant Physiol.*, 93:857-863, 1990.
Hellens et al., "A guide to *Agrobacterium* binary Ti vectors," *Trends in Plant Science*, 5(10):446-451, 2000.
Hellens et al., "pGreen: a versatile and flexible binary Ti vector for *Agrobacterium*-mediated plant transformation," *Plant Molecular Biology*, 42:819-832, 2000.
Hookykaas et al., "The virulence system of *Agrobacterium tumefaciens*," *Ann. Rev. Phytopathol.*, 32:157-179, 1994.
Howard, "The emerging structure of the *Agrobacterium* T-DNA transfer complex," *Bioassays*, 12:103-108, 1990.
Kado, "Molecular mechanisms of crown gall tumorigenesis," *Crit. Rev. Plant Sci.*, 10:1-32, 1991.
Klee et al., "*Agrobacterium*-mediated plant transformation and its further applications to plant biology," *Ann. Rev. Plant Phys.*, 38:467-486, 1987.

(Continued)

*Primary Examiner* — David T Fox
(74) *Attorney, Agent, or Firm* — Dentons US LLP; Dave Lanzotti Esq.

(57) ABSTRACT

Methods and compositions for improved bacterial-mediated plant transformation are provided. The methods generally allow plant transformation with reduced vector backbone integration and a high frequency of low-copy transformation events. Vectors for achieving these results are described, as are methods for their use.

19 Claims, 13 Drawing Sheets

Specification includes a Sequence Listing.

(56) References Cited

OTHER PUBLICATIONS

Kononov et al., "Integration of T-DNA binary vector "backbone" sequences into the tobacco genome: evidence for multiple complex patterns of integration," *Plant J.* May:11(5); 945-47; 1997.

Lessl et al., "Common mechanisms in bacterial conjugation and Ti-mediated T-DNA transfer to plant cells," *Cell*, 77:321-324, 1994.

Matzke et al., "Position effects and epigenetic silencing of plant transgenes," Current Opinion in *Plant Biology*, 1:142-148, 1998.

McBride et al., "Improved binary vectors for agrobacterium-mediated plant transformation," *Plant Molecular Biology*, 14:269-276, 1990.

Nishiguchi et al., "Characterization and sequence determination of the replicator region in the hairy-root inducing plasmid pRiA 4b," *Mol. Gen. Genet.*, 206:1-8, 1987.

Oltmanns et al., "Generation of Backbone-free, Low Transgene Copy Plants by Launching T-DNA from the *Agrobacterium* Chromosome," *Plant Physiology*, 152:1158-1166; 2010.

Ream, "*Agrobacterium tumefaciens* and interkingdom genetic exchange," *Ann. Rev. Phytopathol.*, 27:583-618, 1989.

Rogers et al., "Improved vectors for plant transformation: expression cassette vectors and new selectable markers," *Methods Enzymol.*, 153:253-277, 1987.

Shimamoto et al., "Fertile transgenic rice plants regenerated from transformed protoplasts," *Nature*, 338:274-276, 1989.

Simoens et al., "A binary vector for transferring genomic libraries to plants," *Nucleic Acids Research*, 14(20):8073-8090, 1986.

Tinland et al., "*Agrobacterium tumefaciens* transfers single-stranded transferred DNA (T-DNA) into the plant cell nucleus," *Proc. Natl. Acad.Sci.*, 91:8000-8004, 1994.

Vasil et al., "Herbicide resistant fertile transgenic wheat plants obtained by microprojectile bombardment of regenerable embryonic callus," *Bio/Technology*, 10:667-674, 1992.

Vasil et al., "Regeneration of plants from embryogenic suspension culture protoplasts of wheat (*Triticum aestivum* L.)," *Bio/Technology*, 8:429-434, 1990.

Winans, "Two-way chemical signaling in agrobacterium-plant interactions," *Microbiol. Rev.*, 56-12-31, 1992.

Ye et al., "Enhanced Production of Single Copy Backbone-Free Transgenic Plants in Multiple Crop Species Using Binary Vectors with a pRi Replication Origin in *Agrobacterium tumefaciens*," Transgenic Res., 20:773-786, 2011.

Zambryski, "Chronicles from the *Agrobacterium*-plant cell DNA transfer story," *Ann. Rev. Plant Physiol. Plant Mol. Biol.*, 43:465-490, 1992.

Zupan et al., "Transfer of T-DNA from *Agrobacterium* to the plant cell," *Plant Physiol.*, 107:1041-1047, 1995.

\* cited by examiner

SEQUENCE LISTING

<160> NUMBER OF SEQ ID NOS: 44

<210> SEQ ID NO 1
<211> LENGTH: 7299

```
<212> TYPE: DNA
<213> ORGANISM: Agrobacterium rhizogenes

<400> SEQUENCE: 1
agatcctaca aggtagaatc cgcctgagtc gcaagggtga cttcgcctat attggacgac     60
ggcgcgcaga gggcgacctc tttttgggtt acgattgtag gattatcact aaaacaatac    120
atgaacatat tcaaatggca atctctctaa ggcattggaa ataaatacaa ataacagttg    180
ggtggagttt ttcgacctga gggcgttaac cttctgttaa cctaaaagct cttgcccaaa    240
cagcagaatc ggcgctaatt gccagcggcg gaacttttcc agtttcgcga aaatatcgc     300
cactggcaag gaatgggttt gagatggcga agtctgtcct aaaagcagcg cctgtagttg    360
tagggttgac ggccttgatg gagcgtcatg ccgatgccct ctcgagccaa cttcaagcac    420
atcatcttaa ggttttcccg ccgcattccg agaagggcat tcgaacattc gggccatcgg    480
aggcgtccaa gctgctcggc gttggcgagt catatttacg gcagaccgcg tctgagatgc    540
cagagttgaa tgttagcatg agcccgggtg gcaggcgaat gttctcaatt gaagatatcc    600
atgtgattcg gaagtatatg gatcaggtcg gccgcgggaa ccggcgctac ctgccacatc    660
gtcgaggcgg cgagcagctt caggttatct ctgtgatgaa tttcaaaggt gggtcgggta    720
agaccaccac cgccgcgcat ctggcgcagt acctcgctat gcgcggatat cgagtcttgg    780
ccattgatct cgatcctcaa gcgagccttt ctgcactctt tgggagccaa ccggagacgg    840
acgttggccc gaacgaaacg ctctacggcg ctataaggta tgatgatgag caggtggcaa    900
tcgaacgagt cgtccgaggg acttacattc ccgacctcca cctgattcct ggtaaccttg    960
agctgatgga gtttgaacac gatacgccac gcgcgctgat gaaccgcaaa gagggcgaca   1020
cgctcttttta tggtcgcatc agccaagtaa ttgaagatat cgcggataac tatgacgtcg   1080
tggtcatcga ctgccctccc cagcttgggt atctcacgct atccgcattg actgcggcga   1140
cgtccattct tgtcacggtc catccgcaga tgctggatgt gatgtcgatg aaccagtttc   1200
tggcaatgac atcgaacctt ttgcgtgaaa tcgagaatgc tggcgccaag ttcaagttta   1260
attggatgcg ctatctgata acccgtttcg aaccgagcga cggaccacag aaccaaatgg   1320
taggttatct gcggtcgatt tttggcgaaa atgtcctcaa ttttccgatg cttaaaacca   1380
ccgcggtttc ggacgctggc ctgacaaacc agactctatt cgaagtggag cgtggcctgt   1440
tcacgcgctc gacctatgat cgagccttgg aggcgatgaa cgccgtcaac gacgagatcg   1500
aaacactgat caaaaagca tggggtaggc ccacatgagc cggaagcaca tccttggcgt   1560
ctcaactgac gccccctgaga cgtcgcccgc cgacaatagg acggcaaaga accgctccat   1620
gccgctcctc ggcgtaacaa ggaaggagcg cgatccggca acgaagctca cagcgaacat   1680
tggtaacgca ctgcgagagc aaaacgatcg tcttagccgt gccgaagaga tcgagcggcg   1740
tctcgctgaa ggtcaggcag tgatagagtt ggatgcctcg tcaatagaac cgtctttcgt   1800
gcaggatcgt atgcgagggg acattgacgg gctccttact tcgatccggg aacaaggaca   1860
gcaagtccca atccttgtgc gaccgcatcc gagccagccg ggccgatatc aggttgcctt   1920
cggccaccgc cggctacgcg ccgtttcaga actcggactt ccggtcagag cggtcgttcg   1980
cgaactgacg gacgagcaag tggtcgtagc acagggtcag gaaaacaatg agcgcgaaga   2040
tcttaccttc atcgaaaagg cgcgcttcgc acatcgcctg aacaggcagt tttctcgaga   2100
gattgtcatc gccgcgatgt cgatcgacaa gagcaatttg tccaagatgc ttctgctcgt   2160
cgacgccctc ccctctgaac tgaccgatgc tattggtgcc gctcctggtg ttggacggcc   2220
```

```
gagttggcaa caacttgccg agctgattga gaaagtttct tcaccggccg acgtggctaa    2280
atatgctatg tcggaggaag ttcaagcgct gccatcggca gaacgattca aggcggtgat    2340
cgctagtctg aagcccagtc gggttgcgcg tggacttccc gaggtcatgg ccaccccaga    2400
cggcaccaga attgcacagg tgacgcagag caaggccaaa ctggaaatca cgattgacag    2460
gaaggcgacg cccgattttg cgaccttcgt gctcgatcat gtgccagcgc tgtatcaagc    2520
gtaccacgct gagaaccaac ggaaacgggg agagtaaacc gcaaaagaaa agagcccct    2580
caacgtcgcc gtcgcggaag cccttctgtc tctctagcgc gaacagaatc gcatttcctc    2640
gaatcctcgt caagagtttt tagcgccgtt ttggtgagct gatttccttt gcctgctgaa    2700
aggtgaaaga tgatgcagac aggaagtgta acgacgccat cgggcggcg gccaatgacg     2760
cttgcgcttg tgcggcgcca gacgcgctg gccgatatca aacaaggcaa acagcggac     2820
aagtggaagg tctttagaga cgcgtccgcg gccatggaac tacttggaat ccagtccaac    2880
agtcttgccg tccttgatgc gctattgagc tttcacccgg aaacggagtt gcgtcaggag    2940
gcacagctga tcgtcttccc gtcgaatgct cagcttgccc ttcgggcgca tgggatggct    3000
ggcgcgactt tgcgtaggca catcgccatg ctcgtggagt caggcttgat cgtccggaag    3060
gatagcgcca acgaaaagcg ttacgctcgt aaggatggcg ctggtcagat cgagcgcgcg    3120
tttggcttcg atttgtctcc gcttctcgcg cggtccgaag agctagcgat gatggcacag    3180
caggtgatgg ccgatcgagc agcattcagg atggccaaaa aaagtctgac gatttgccga    3240
cgggacgttc ggaagctaat tacggcagct atggaagagg gagcggaggg cgactggcaa    3300
gctgtcgagg aagtctatgt ggaacttgtg ggtagaattc cacgcgcccc gacgcttgct    3360
gatgtagagt caattctcga agagatgtgg atgctccagg aagagataat caaccggttg    3420
gaaattagag acaattcaga aaataatagc accaatgctg cccagagcga gcagcacata    3480
cagaattcaa aacccgaatc cgttaatgaa cttgaacctc gctctgaaaa ggagcagggc    3540
gctaagccga gtgaaataga ccgggcaagg agcgagccga taaaagcgtt cccctcggg    3600
atgatcctga aagcatgccc gaccattggc aattatgggc cgagcggtgc ggttgctagc    3660
tggcgtgacc tcatgtcggc tgcggtggtg gttcggtcta tgctgggggt cagcccgtcg    3720
gcttaccaag acgcgtgtga ggcaatggga ccggagaatg cggcagcagc gatggcgtgc    3780
atttggagc gagcgaactt catcaattcg cccgggggct atctccgaga tctgacacgg    3840
cggagcgagc tcgggaagtt ttcacttggc ccgatgataa tggcgctctt gaaggctagc    3900
gggcagggga cgttgcggtt tggctagaat tagcgagtat ggagcaggat ggtctgtggt    3960
cagctgacca cagacctaat aggttgaaaa catgagcgtt ttttggatga tcgacagacc    4020
atccgattcc cggagtacca agcgtgctct gatgggagcg ataacattac tcaacaagca    4080
cgaaggcccc atgccgatcg ttgatcgtga aggagagcct gctctacatg cggcggtatt    4140
ttgccggccg aggcatgtag tcgcggagca ctgcctattt actgccctag cacaaacgt     4200
tgactcttgg atcgagctgg cagacaaagc aataacccac acagaggacg attaatggct    4260
gacgaagaga tccagaatcc gccggacggt actgctgctg ccgaagttga gccggctgct    4320
cctagaggta gaagagcaaa gaaagcacca gccgaaacag cccgcacggg atcgttcaaa    4380
tccgtgaagc cgaaaacccg cggcctcagc aaccgagaaa aactggagaa gatcggtcaa    4440
atcgaagctc aggtcgctgg cggcgcaacc ttgaaggacg ccgttaagat cgtgggtatt    4500
tccgttcaga cctattatca atggaagaga gctgcggttc aacctgtctc acagaatccg    4560
gccgtgtctg tttcagttga cgatgaactc ggcgagttca tccaactcga ggaggaaaat    4620
```

-continued

```
cggcggctca gaaagctagc ttctctctga aaaattgcgc gcagaaaacg cggacttacg   4680
caaaagactt ggaatcaact agcggccttt gggggtccct cgctaaatca acttgacgcg   4740
catctctcaa tgaatgaatg ccttggaaaa tttccgcgca ttctgatcgt tgcgctatca   4800
agcaatccca atcttctggc atatgaaaaa accacgaccc aaattcgtcg tcgaatataa   4860
gacgaacagg cgacaagcca aggcccgacc aacgtcaatc tggggcaatc tgggtttgca   4920
ggcggtgggc cgtgcggtcg cggccgacgg agtcgtgccg aagagtagtc tgccgcaagt   4980
ccgttccgtc ctggagaagg ttgtcgcgtc caaggttacc gtcgtggtcc ctcggtgctg   5040
ccaggttttg aggaagagct tgccgctatc gaggcgaaaa accgtcgtct gaagcgcctc   5100
ttgatcgtga agctccgtga ggagaacgac aggcttaagt tcgcgcttcg acgatttggg   5160
ggcgcctgag cacgatgctg gcccacttgc ttcagcgggc aaacaacatg gagtggagat   5220
ctaatgatcg cggcgcttga acatcgctag gggtcttcgg cgccgctgaa ccgtgctcca   5280
ttttgcactc ggagacacag cctcccaaaa cctggcgcc gctcgttggt gaactcctca   5340
acatcgagcg gatcaaggga aactggaatg acatccttcg acccgtcacg gcgatccgct   5400
ctggccaggt ccaacctacg gccatgcccg caaagccaac ggcatttcca cgtcaagcac   5460
attgacccac tcggctgacg gtacatcagc tggcgagctc atccggaccc agacgaactg   5520
cgttgatctc aggccgttgc ggcagaaaac ctccatcctc gcagccgatc caacactttc   5580
ctgtggtaat gcctatttca gatgaaacag cctttttaa acttggcgcg tcattctgat   5640
attatggcca cacctctacg atctagggag tgcgagaagt ggaaagaaat gaagaacccg   5700
atttgcacac acataccgcg atgcggaata aaaatgcatc atcgcttggt gaggccctgg   5760
atgacgatgc gatcgccaac atcgcgcatc acattgttac agacgacccg gtggaaacgt   5820
caaaaaactt cacaaaactt aagctgatta acaaatcagt gaaacagggt ttcgaacgca   5880
gtgcgtacgg aaaattccat cgacgcatta gccggcttgg tattgctagt aaggcgctat   5940
atgacaacgc tgtgccgaag gaaggattcg tagaacatcc tgaatatgct ccagctctgc   6000
aaagggatta tgcgttggca ggagagcgaa ttgaggcggt tggtggaact ttcaggttgc   6060
aaacacctca gcggaaatcg gctcttgtag atcatatctt gagtatgccc gaaggtttcg   6120
atcaagctca tgcccttgag tctatagccc ctcatgttgg cgatctaagc gcggaagatc   6180
gccatcgtgt tgtgaacaaa atgctcgagc actttgccac cccgtttcaa gaagggggc   6240 tgccaaccga cgaaaatttt tgtggaacgt acgctttgtc caaggcgttt cctcatatgg   6300
aagacagcct aaaagcaaag atgctggatg tggtgttaga gcatcctcac ttagccaacc   6360
tccattggac gcagagagaa ctagttgaag ggtggcatca agaccgtgaa gctgagaagt   6420
cagcctggcg ttccaatcaa aagccaattg tcgaggggcg acttcagac ctcgaacgat   6480 cgatccacag tgatatcgag gtgacaaaca ggagtgattt tgcgaggatg cgttcagcca   6540
ggcccttgca acaagctata agcgatacgt tcgatcttgc gcgtgaggag ctcaaaagcc   6600
gccctcgtga agggcgggt cgataattac atctattggt ctttctgccg aacctctatg   6660
aaatccgcac gtcaaatgtg gcttttactt cccgatttca attgaagcgc taagctgaaa   6720
atcccgtccc catttctgac ctaacggttt catcaccggg gcagggagcg cgcttaaaa   6780 cggtgacggc caccaccaaa ggacatgttc gctcacgcgg tgcctccgtg cttctttgca   6840
agagcctgct tcaggctgat gatctccttc agtgcgttgg tgtgaatccg ctccaggcgt   6900
ttcagttcgc tctccaaata ggcgttgcgc ttatccagcc tcgtccgatc ttcttccaag   6960
```

```
ctctccattt tcactagcgc gttatggtaa ttcaaccgta actcctcaaa aaaagcacgt      7020
tcggcgacga atgggtttc ggaatcgagt tcaggtatgt cgccgacatg cacgacgcga       7080
accgccttgc cggcagcggc gagccgggcg cggtaagcgc gttgaatttc cgcttgggtc      7140
agcgcgtttg gcttgcgggg ccgcgaggaa atttgggagt aaccataacg gttatttatc      7200
ataacgcgtt atcactggat agcatcggcg caggcggatg gcgcgcttcg ccgggtcgaa      7260
atcaatattt ccagatcgag atggattgaa gacctgaag                             7299
```

```
<210> SEQ ID NO 2
<211> LENGTH: 5617
<212> TYPE: DNA
<213> ORGANISM: Agrobacterium rhizogenes

<400> SEQUENCE: 2
```

```
agatcctaca aggtagaatc cgcctgagtc gcaagggtga cttcgcctat attggacgac        60
ggcgcgcaga gggcgacctc tttttgggtt acgattgtag gattatcact aaaacaatac       120
atgaacatat tcaaatggca atctctctaa ggcattggaa ataaatacaa ataacagttg       180
ggtggagttt ttcgacctga gggcgttaac cttctgttaa cctaaaagct cttgcccaaa       240
cagcagaatc ggcgctaatt gccagcggcg gaacttttcc agtttcgcga aaatatcgc        300 cactggcaag gaatgggttt gagatggcga agtctgtcct aaaagcagcg cctgtagttg       360
tagggttgac ggccttgatg gagcgtcatg ccgatgccct ctcgagccaa cttcaagcac       420
atcatcttaa ggttttcccg ccgcattccg agaagggcat tcgaacattc gggccatcgg       480
aggcgtccaa gctgctcggc gttggcgagt catatttacg gcagaccgcg tctgagatgc       540
cagagttgaa tgttagcatg agcccgggtg gcaggcgaat gttctcaatt gaagatatcc       600
atgtgattcg gaagtatatg gatcaggtcg gccgcgggaa ccggcgctac ctgccacatc       660
gtcgaggcgg cgagcagctt caggttatct ctgtgatgaa tttcaaaggt gggtcgggta      720
agaccaccac cgccgcgcat ctggcgcagt acctcgctat gcgcggatat cgagtcttgg      780
ccattgatct cgatcctcaa gcgagccttt ctgcactctt tgggagccaa ccggagacgg      840
acgttggccc gaacgaaacg ctctacgcg ctataaggta tgatgatgag caggtggcaa       900
tcgaacgagt cgtccgaggg acttacattc ccgacctcca cctgattcct ggtaaccttg      960
agctgatgga gtttgaacac gatacgccac gcgcgctgat gaaccgcaaa gagggcgaca     1020
cgctctttta tggtcgcatc agccaagtaa ttgaagatat cgcggataac tatgacgtcg     1080
tggtcatcga ctgccctccc cagcttgggt atctcacgct atccgcattg actgcggcga     1140
cgtccattct tgtcacggtc catccgcaga tgctggatgt gatgtcgatg aaccagtttc     1200
tggcaatgac atcgaacctt tgcgtgaaa tcgagaatgc tggcgccaag ttcaagttta      1260
attggatgcg ctatctgata acccgtttcg aaccgagcga cggaccacag aaccaaatgg     1320
taggttatct gcgtcgatt tttggcgaaa atgtcctcaa ttttccgatg cttaaaacca      1380 ccgcggttc ggacgctggc ctgacaaacc agactctatt cgaagtggag cgtggcctgt      1440
tcacgcgctc gacctatgat cgagccttgg aggcgatgaa cgccgtcaac gacgagatcg     1500
aaacactgat caaaaaagca tggggtaggc ccacatgagc cggaagcaca tccttggcgt     1560
ctcaactgac gcccctgaga cgtcgcccgc cgacaatagg acggcaaaga accgctccat     1620
gccgctcctc ggcgtaacaa ggaaggagc cgatccggca acgaagctca cagcgaacat      1680
tggtaacgca ctgcgagagc aaaacgatcg tcttagccgt gccgaagaga tcgagcggcg     1740
tctcgctgaa ggtcaggcag tgatagagtt ggatgcctcg tcaatagaac cgtctttcgt     1800
```

```
gcaggatcgt atgcgagggg acattgacgg gctccttact tcgatccggg aacaaggaca    1860
gcaagtccca atccttgtgc gaccgcatcc gagccagccg ggccgatatc aggttgcctt    1920
cggccaccgc cggctacgcg ccgtttcaga actcggactt ccggtcagag cggtcgttcg    1980
cgaactgacg gacgagcaag tggtcgtagc acagggtcag gaaaacaatg agcgcgaaga    2040
tcttaccttc atcgaaaagg cgcgcttcgc acatcgcctg aacaggcagt tttctcgaga    2100
gattgtcatc gccgcgatgt cgatcgacaa gagcaatttg tccaagatgc ttctgctcgt    2160
cgacgccctc ccctctgaac tgaccgatgc tattggtgcc gctcctggtg ttggacggcc    2220
gagttggcaa caacttgccg agctgattga gaaagtttct tcaccggccg acgtggctaa    2280
atatgctatg tcggaggaag ttcaagcgct gccatcggca gaacgattca aggcggtgat    2340
cgctagtctg aagcccagtc gggttgcgcg tggacttccc gaggtcatgg ccaccccaga    2400
cggcaccaga attgcacagg tgacgcagag caaggccaaa ctggaaatca cgattgacag    2460
gaaggcgacg cccgattttg cgaccttcgt gctcgatcat gtgccagcgc tgtatcaagc    2520
gtaccacgct gagaaccaac ggaaacgggg agagtaaacc gcaaagaaa agagccccct    2580 caacgtcgcc gtcgcggaag cccttctgtc tctctagcgc gaacagaatc gcatttcctc    2640
gaatcctcgt caagagtttt tagcgccgtt ttggtgagct gatttccttt gcctgctgaa    2700
aggtgaaaga tgatgcagac aggaagtgta acgacgccat cgggcggcg gccaatgacg    2760 cttgcgcttg tgcggcgcca gacggcgctg gccgatatca aacaaggcaa gacagcggac    2820
aagtggaagg tctttagaga cgcgtccgcg gccatggaac tacttggaat ccagtccaac    2880
agtcttgccg tccttgatgc gctattgagc tttcacccgg aaacggagtt gcgtcaggag    2940
gcacagctga tcgtcttccc gtcgaatgct cagcttgccc ttcgggcgca tgggatggct    3000
ggcgcgactt tgcgtaggca catcgccatg ctcgtggagt caggcttgat cgtccggaag    3060
gatagcgcca acggaaagcg ttacgctcgt aaggatggcg ctggtcagat cgagcgcgcg    3120
tttggcttcg atttgtctcc gcttctcgcg cggtccgaag agctagcgat gatggcacag    3180
caggtgatgg ccgatcgagc agcattcagg atggccaaag aaagtctgac gatttgccga    3240
cgggacgttc ggaagctaat tacggcagct atggaagagg gagcggaggg cgactggcaa    3300
gctgtcgagg aagtctatgt ggaacttgtg ggtagaattc cacgcgcccc gacgcttgct    3360
gatgtagagt caattctcga agagatgtgg atgctccagg aagagataat caaccggttg    3420
gaaattagag acaattcaga aaataatagc accaatgctg cccagagcga gcagcacata    3480
cagaattcaa aacccgaatc cgttaatgaa cttgaacctc gctctgaaaa ggagcagggc    3540
gctaagccga gtgaaataga ccgggcaagg agcgagccga taaaagcgtt cccctcggg    3600 atgatcctga aagcatgccc gaccattggc aattatgggc cgagcggtgc ggttgctagc    3660
tggcgtgacc tcatgtcggc tgcggtggtg gttcggtcta tgctgggggt cagcccgtcg    3720
gcttaccaag acgcgtgtga ggcaatggga ccggagaatg cggcagcagc gatggcgtgc    3780
attttggagc gagcgaactt catcaattcg cccgggggct atctccgaga tctgacacgg    3840
cggagcgagc tcgggaagtt ttcacttggc ccgatgataa tggcgctctt gaaggctagc    3900
gggcagggga cgttgcggtt tggctagaat tagcgagtat ggagcaggat ggtctgtggt    3960
cagctgacca cagacctaat aggttgaaaa catgagcgtt ttttggatga tcgacagacc    4020
atccgattcc cggagtacca agcgtgctct gatgggagcg ataacattac tcaacaagca    4080
cgaaggcccc atgccgatcg ttgatcgtga aggagagcct gctctacatg cggcggtatt    4140
```

```
ttgccggccg aggcatgtag tcgcggagca ctgcctattt actgccctag gcacaaacgt    4200
tgactcttgg atcgagctgg cagacaaagc aataacccac acagaggacg attaatggct    4260
gacgaagaga tccagaatcc gccggacggt actgctgctg ccgaagttga gccggctgct    4320
cctagaggta gaagagcaaa gaaagcacca gccgaaacag cccgcacggg atcgttcaaa    4380
tccgtgaagc cgaaaacccg cggcctcagc aaccgagaaa aactggagaa gatcggtcaa    4440
atcgaagctc aggtcgctgg cggcgcaacc ttgaaggacg ccgttaagat cgtgggtatt    4500
tccgttcaga cctattatca atggaagaga gctgcggttc aacctgtctc acagaatccg    4560
gccgtgtctg tttcagttga cgatgaactc ggcgagttca tccaactcga ggaggaaaat    4620
cggcggctca gaaagctagc ttctctctga aaaattgcgc gcagaaaacg cggacttacg    4680
caaaagactt ggaatcaact agcggccttt ggggtccct cgctaaatca acttgacgcg     4740
catctctcaa tgaatgaatg ccttggaaaa tttccgcgca ttctgatcgt tgcgctatca    4800
agcaatccca atcttctggc atatgaaaaa accacgaccc aaattcgtcg tcgaatataa    4860
gacgaacagg cgacaagcca aggcccgacc aacgtcaatc tggggcaatc tgggtttgca    4920
ggcggtgggc cgtgcggtcg cggccgacgg agtcgtgccg aagagtagtc tgccgcaagt    4980
ccgttccgtc ctggagaagg ttgtcgcgtc caaggttacc gtcgtggtcc ctcggtgctg    5040
ccaggttttg aggaagagct tgccgctatc gaggcggaaa accgtcgtct gaagcgcctc    5100
ttgatcgtga agctccgtga ggagaacgac aggcttaagt tcgcgcttcg acgatttggg    5160
ggcgcctgag cacgatgctg gcccacttgc ttcagcgggc aaacaacatg gagtggagat    5220
ctaatgatcg cggcgcttga acatcgctag gggtcttcgg cgccgctgaa ccgtgctcca    5280
ttttgcactc ggagacacag cctcccaaaa acctggcgcc gctcgttggt gaactcctca    5340
acatcgagcg gatcaaggga aactggaatg acatccttcg acccgtcacg gcgatccgct    5400
ctggccaggt ccaacctacg gccatgcccg caaagccaac ggcatttcca cgtcaagcac    5460
attgacccac tcggctgacg gtacatcagc tggcgagctc atccggaccc agacgaactg    5520
cgttgatctc aggccgttgc ggcagaaaac ctccatcctc gcagccgatc caacactttc    5580
ctgtggtaat gcctatttca gatgaaacag ccttttt                             5617
```

<210> SEQ ID NO 3
<211> LENGTH: 4115
<212> TYPE: DNA
<213> ORGANISM: Agrobacterium rhizogenes

<400> SEQUENCE: 3

```
tacaaggtag aatccgcctg agtcgcaagg gtgacttcgc ctatattgga cgacggcgcg      60
cagagggcga cctctttttg ggttacgatt gtaggattat cactaaaaca atacatgaac     120
atattcaaat ggcaatctct ctaaggcatt ggaaataaat acaataaca gttgggtgga     180 gtttttcgac ctgagggcgt taaccttctg ttaacctaaa agctcttgcc caaacagcag    240
aatcggcgct aattgccagc ggcggaactt ttccagtttc gcgaaaaata tcgccactgg    300
caaggaatgg gtttgagatg gcgaagtctg tcctaaaagc agcgcctgta gttgtagggt    360
tgacggcctt gatggagcgt catgccgatg ccctctcgag ccaacttcaa gcacatcatc    420
ttaaggtttt cccgccgcat tccgagaagg gcattcgaac attcgggcca tcggaggcgt    480
ccaagctgct cggcgttggc gagtcatatt tacggcagac cgcgtctgag atgccagagt    540
tgaatgttag catgagcccg ggtggcaggc gaatgttctc aattgaagat atccatgtga    600
ttcggaagta tatggatcag gtcggccgcg ggaaccggcg ctacctgcca catcgtcgag    660
```

```
gcggcgagca gcttcaggtt atctctgtga tgaatttcaa aggtgggtcg ggtaagacca      720
ccaccgccgc gcatctggcg cagtacctcg ctatgcgcgg atatcgagtc ttggccattg      780
atctcgatcc tcaagcgagc ctttctgcac tctttgggag ccaaccggag acggacgttg      840
gcccgaacga aacgctctac ggcgctataa ggtatgatga tgagcaggtg gcaatcgaac      900
gagtcgtccg agggacttac attcccgacc tccacctgat tcctggtaac cttgagctga      960
tggagtttga acacgatacg ccacgcgcgc tgatgaaccg caaagagggc gacacgctct     1020
tttatggtcg catcagccaa gtaattgaag atatcgcgga taactatgac gtcgtggtca     1080
tcgactgccc tccccagctt gggtatctca cgctatccgc attgactgcg gcgacgtcca     1140
ttcttgtcac ggtccatccg cagatgctgg atgtgatgtc gatgaaccag tttctggcaa     1200
tgacatcgaa ccttttgcgt gaaatcgaga atgctggcgc caagttcaag tttaattgga     1260
tgcgctatct gataacccgt ttcgaaccga gcgacggacc acagaaccaa atggtaggtt     1320
atctgcggtc gattttggc gaaaatgtcc tcaattttcc gatgcttaaa accaccgcgg      1380
tttcggacgc tggcctgaca accagactc tattcgaagt ggagcgtggc ctgttcacgc      1440
gctcgaccta tgatcgagcc ttggaggcga tgaacgccgt caacgacgag atcgaaacac     1500
tgatcaaaaa agcatggggt aggcccacat gagccggaag cacatccttg gcgtctcaac     1560
tgacgcccct gagacgtcgc ccgccgacaa taggacggca agaaccgct ccatgccgct      1620 cctcggcgta caaggaagg agcgcgatcc ggcaacgaag ctcacagcga acattggtaa      1680
cgcactgcga gagcaaaacg atcgtcttag ccgtgccgaa gagatcgagc ggcgtctcgc     1740
tgaaggtcag gcagtgatag agttggatgc ctcgtcaata gaaccgtctt tcgtgcagga     1800
tcgtatgcga ggggacattg acgggctcct tacttcgatc cgggaacaag gacagcaagt     1860
cccaatcctt gtgcgaccgc atccgagcca gccgggccga tatcaggttg ccttcggcca     1920
ccgccggcta cgcgccgttt cagaactcgg acttccggtc agagcggtcg ttcgcgaact     1980
gacggacgag caagtggtcg tagcacaggg tcaggaaaac aatgagcgcg aagatcttac     2040
cttcatcgaa aaggcgcgct cgcacatcg cctgaacagg cagttttctc gagagattgt      2100
catcgccgcg atgtcgatcg acaagagcaa tttgtccaag atgcttctgc tcgtcgacgc     2160
cctcccctct gaactgaccg atgctattgg tgccgctcct ggtgttggac ggccgagttg     2220
gcaacaactt gccgagctga ttgagaaagt ttcttcaccg gccgacgtgg ctaaatatgc     2280
tatgtcggag gaagttcaag cgctgccatc ggcagaacga ttcaaggcgg tgatcgctag     2340
tctgaagccc agtcgggttg cgcgtggact tcccgaggtc atggccaccc cagacggcac     2400
cagaattgca caggtgacgc agagcaaggc caaactggaa atcacgattg acaggaaggc     2460
gacgcccgat tttgcgacct tcgtgctcga tcatgtgcca cgcgctgtatc aagcgtacca     2520 cgctgagaac caacggaaac ggggagagta aaccgcaaaa gaaagagcc ccctcaacgt      2580 cgccgtcgcg gaagcccttc tgtctctcta gcgcgaacag aatcgcattt cctcgaatcc     2640
tcgtcaagag ttttagcgc cgttttggtg agctgatttc ctttgcctgc tgaaaggtga      2700
aagatgatgc agacaggaag tgtaacgacg ccattcgggc ggcggccaat gacgcttgcg     2760
cttgtgcggc gccagacggc gctggccgat atcaaacaag gcaagacagc ggacaagtgg     2820
aaggtcttta gagacgcgtc cgcggccatg gaactacttg gaatccagtc caacagtctt     2880
gccgtccttg atgcgctatt gagctttcac ccggaaacgg agttgcgtca ggaggcacag     2940
ctgatcgtct tcccgtcgaa tgctcagctt gcccttcggg cgcatgggat ggctggcgcg     3000
```

```
actttgcgta ggcacatcgc catgctcgtg gagtcaggct tgatcgtccg gaaggatagc    3060
gccaacggaa agcgttacgc tcgtaaggat ggcgctggtc agatcgagcg cgcgtttggc    3120
ttcgatttgt ctccgcttct cgcgcggtcc gaagagctag cgatgatggc acagcaggtg    3180
atggccgatc gagcagcatt caggatggcc aaagaaagtc tgacgatttg ccgacgggac    3240
gttcggaagc taattacggc agctatggaa gagggagcgg agggcgactg gcaagctgtc    3300
gaggaagtct atgtggaact tgtgggtaga attccacgcg ccccgacgct tgctgatgta    3360
gagtcaattc tcgaagagat gtggatgctc caggaagaga taatcaaccg gttggaaatt    3420
agagacaatt cagaaaataa tagcaccaat gctgcccaga gcgagcagca catacagaat    3480 tcaaacccg aatccgttaa tgaacttgaa cctcgctctg aaaaggagca gggcgctaag    3540
ccgagtgaaa tagaccgggc aaggagcgag ccgataaaag cgttcccct cgggatgatc    3600 ctgaaagcat gcccgaccat tggcaattat gggccgagcg gtgcggttgc tagctggcgt    3660
gacctcatgt cggctgcggt ggtggttcgg tctatgctgg gggtcagccc gtcggcttac    3720
caagacgcgt gtgaggcaat gggaccggag aatgcgcag cagcgatggc gtgcattttg    3780
gagcgagcga acttcatcaa ttcgcccggg ggctatctcc gagatctgac acggcggagc    3840
gagctcggga agttttcact tggcccgatg ataatgcgc tcttgaaggc tagcgggcag    3900
gggacgttgc ggtttggcta gaattagcga gtatggagca ggatggtctg tggtcagctg    3960
accacagacc taataggttg aaaacatgag cgttttttgg atgatcgaca gaccatccga    4020
ttcccggagt accaagcgtg ctctgatggg agcgataaca ttactcaaca agcacgaagg    4080
ccccatgccg atcgttgatc gtgaaggaga gcctg                              4115
```

<210> SEQ ID NO 4
<211> LENGTH: 4304
<212> TYPE: DNA
<213> ORGANISM: Rhizobium etli

<400> SEQUENCE: 4

```
agttacggct gatcgaccag acccggcacc ttaccgccgc gccccgctcc atccacgcca      60
gcgaaccgat gccttgcatc tgcgggcttg cagcaaggcg cttgcacgc ccgacattgc     120 gattcggatt atactgctgc tgttcccggc cggtctcgtc cgattcggcc tgtgaatgtg     180
cgattgctgg acccgccagc ggcacgcccg gccggcgcaa gcgcttgaaa tagactggac     240 aacccttttga taggatcttg ttaaccctat ttgccttgcc accctccag aatcggcgct     300 aaatgcggtt tcaaagcgcg tagagctttt aaatcgcatt ttcgagattt ccatgaatat     360
ggcaccgcaa atagaaaaag caatttccga tgtcgaccag ctgatcatcg gtcaggcaca     420
ggaactatcc gacaagctga agcagcatcg cctcgaaatg tttcctccgc gcgcgctaaa     480
gggtctgcgg gaatttcagc ttgctgaagt ggcgcggttt ctcggcgtga ccagcggcta     540
tcttcgaaat ctttcgctcg agggcaaggg tgccctcccc caggttacgc cgtctggccg     600
ccgatcgtat acgcggagc agatggagga gatgcgtggc tttctcgagc ataatgcgcg     660
cgccggaaca cattatgtgc gtcatcgccg cggccacgaa catctgcagg tcgttgctgt     720
cgtcaacttc aaggggggca gcggcaagac gacgagtgcc gcgcatcttg cccagcatct     780
cgccctgacc ggtcaccgcg tcctggccgt cgatctcgat ccgcaagcgt ctctttctgc     840
catacacggc tttcagccgg agttcgacgt caacgaaaac gagacactct acgccgccat     900
tcgctatgac gatcagcggc gtccgctgcg ggacattatc cggccgacca acttcccgaa     960
ccttcatctc gtgccgggca atctcgaact gatggaattc gagcacgata cgccgcgggt    1020
```

```
cctcgctcag ggcaaagcga gcgattatgg gcgcgtcttc tttgcccggc tggatgaggc    1080
gctggcctcg gtcgcggatg attacgacgt cgtcatcatc gattgccctc cccagcttgg    1140 cttttttgacc atgagcgcca tttgcggtgc gacggcggtt ctgatcaccg ttcatccgca    1200
gatgctcgat gtcatgtcga tgtgccagtt cctgcaaatg cttggcgaag tgctgaacac    1260
gctgaaggga gccggcggca atatgaacct cgactggctg cgttacctcg tgacccgcta    1320
cgatccgcag gacgggccgc agacgcagat ggtcgcctcc atgcgctcga tgttcaagag    1380
ccatgtgctc accaacccga tgctgcgcag cgtcgcgatc tccgatgcgg cgatgactaa    1440
ccagacgctg tacgaagtcg agcgaagtca gtttacccgc gcgacctatg accgcgccat    1500
ggaggcgatg gagtcagtca cacggaaat cgtcgatctc atccataagg catggggccg    1560
gaaatgagcg ggaagtttac tgcggtaaac cggggcaagg agctggttga tggcgcgtaa    1620
aaatcttctg tcgggcctga tggacgattc caagaagttt actgcggtaa caatgagga    1680 tgagccggcc cctcgcgacg agaggcagca tatcacctat aaggggattg gcgcgctcgg    1740
tgcggtcacc cgcagcatcg atgccttggc cgccaaggcc gatgccgcca aggcgatcga    1800
agagcagctg gcgagcggcg agacggtgat cgatctcgac ccggcgctga tcgaagattc    1860
cttcgtgacc gaccggctgg cgcatactga cgaacagttc cgggaattag tcgaggcgat    1920
ccgcctgcgc ggccaggatt caccgatcct tgtgcgcccg catcccgaga gggaggggcg    1980
atatcagatc gcttttggtc atcgtcgtgc gcgggcggca aaggagctcg gccgacctgt    2040
ccgggcggtg gtcaagagac tcgacgaccg cgaccatgtc attgcgcagg ccaggagaa    2100 ttcgaattcg gcacgcgccg atctctcctt catcgagagg acgatgtttg ccgacaagct    2160
cgacacgttg ggtttcgacc gggaaacgat catgtcggca ctcagcgcag acaagacgac    2220
ggtgtccaag atgctgtcgg tcacgaagcg gattccggcc gaagtcctgg ccgcgatcgg    2280
cgtagccaag acgactggcc gcgatcgctg gcatgatctt tcggcgaaat tcgagacgga    2340
aaacatcgca gcccgggcga ttgagttcac cagatcggtg gagttcgaga cggccgagcc    2400
ggacgcccgc ttcgacatgc ttgtcgcctt catcagcagg aaccaacagg cgtcgcccgc    2460
cgccgcagtt cagcccgtgg cgcacgcctg gcagcgccgg gacggagccg tcaaagcgaa    2520
gatcaaggat gatggaaaac agttcaccat cgcgctgaag gcggagaagg catctgcctt    2580
tggcgcctac atcgccagca atctggatcg tctctacgag gcgttcgaga agacacagga    2640
tttgacgaag aacggagatc aataagcaaa agaaaaggcc cccgaacgtt gccgtcgcgg    2700
aagccctctc tgatctagac acccagagaa tcacatttcc gcgaatcata gtcaagagtc    2760
tttggcaccg aatttggtga ggcgtgatct tttgccttga agaaggcgaa gaaaatggaa    2820
agcggaagtg tgacacgccc ttcgggcggc ggccgatgac gttggcatg ttggcaagtc    2880 aggccgctgc ccgaaaaatc gagcccggcc gatcgattga taaatggaaa ctctatcgcg    2940
ccctgtgcga ggccaggccg ctgctcggca ttacagaccg ggcgctttcc atcctgaacg    3000
ccttgctgag cttttatccc aagggagagc tctccgagga aacggcttg gtcgtatttc    3060 cttcgaatac gcagctctct ctgcgcgcgc atggaatggc ggagcagacg atccgtcgcc    3120
acctggcggc gctgatcgag gccggattgc tgatccgcaa ggacagcccg aacggcaagc    3180
gttacgctcg caaggagcag ggcggggaga tccgtgaggc attcggcttc tcgctggcgc    3240
cgctgcttgc gcgcgcggac gagatcgagc ggctggcggc cgagatggca gccgaacgat    3300
tgcagctgca gcggctcaaa gagcgcctga cgctttgcag gcgcgacatc gccaagctca    3360
```

| | |
|---|---|
| tcgagatggc cgtggaagag ggcgcctctg gtgattggag cggggtccac ctgcattttc | 3420 |
| gaggcatcgt cgaacggctg ccgcgctcgc catccttcga gaagattgcc gccgcactcg | 3480 |
| acgaactgga actgttgcgc gaagaaatca ccaatcagtt ggaaatgcag gttaaagctc | 3540 |
| caaatcaaag cggcaatgcc caacattctg agcggcacat acagaattca acccacact | 3600 |
| acactactga acttgaacca cgcttcgaaa cgaagcaggg cgcaacggtg gacgaccaat | 3660 |
| cggaaggttg ggccgagccg agggccagaa tagcgacaca ggaggggaag ggcaggccca | 3720 |
| tgccagctgc aaactcagcc tcggttgccg gcggcgggct caaatccttc ccgctgggcc | 3780 |
| tggtgctgca ggcctgccca gagatcgccc cctatggacc gcagggctcg gtgggcacat | 3840 |
| ggcgcgatct gatggcggcg gctgtcgtcg tgcgctcaat gctcggagtg agcccctcgg | 3900 |
| cctatgaaca ggcctgcgag gtcatggggc ctgaaaatgc ggctaccgtc atagcgtgcg | 3960 |
| tgcttgaaag ggcagggcac atcaattccg ccggtggtta cctccgtgac ctgacccgcc | 4020 |
| gcgccgagag aggcgaattt gccatcggac cgatgttgat ggcgcttgtc cgcaccaatt | 4080 |
| cgccaatcag aggcaagacc ggatgaaaaa tttcgtgtca tctgtccgtg gcgatctatg | 4140 |
| gttaacgaaa ggtgacggaa ataaacaggg tgataacttc ttgttaggat attcttcctt | 4200 |
| tgagatcatg aagttacaag atttttgatt ggcaaggcga gggaaggacc tgatcgacga | 4260 |
| tcggccggcg ttcgctggag aaacggtgcg gttggagttg acgt | 4304 |

<210> SEQ ID NO 5
<211> LENGTH: 28
<212> TYPE: DNA
<213> ORGANISM: Agrobacterium rhizogenes

<400> SEQUENCE: 5

| | |
|---|---|
| cacgtgtaca aggtagaatc cgcctgag | 28 |

<210> SEQ ID NO 6
<211> LENGTH: 27
<212> TYPE: DNA
<213> ORGANISM: Agrobacterium rhizogenes

<400> SEQUENCE: 6

| | |
|---|---|
| gtatacaggc tctccttcac gatcaac | 27 |

<210> SEQ ID NO 7
<211> LENGTH: 30
<212> TYPE: DNA
<213> ORGANISM: Artificial sequence
<220> FEATURE:
<223> OTHER INFORMATION: Description of Artificial Sequence: Synthetic
       Primer

<400> SEQUENCE: 7

| | |
|---|---|
| agcttgggcc cctcgaggct agcactagtg | 30 |

<210> SEQ ID NO 8
<211> LENGTH: 29
<212> TYPE: DNA
<213> ORGANISM: Artificial sequence
<220> FEATURE:
<223> OTHER INFORMATION: Description of Artificial Sequence: Synthetic
       Primer

<400> SEQUENCE: 8

| | |
|---|---|
| gatccactag tgctagcctc gaggggccc | 29 |

```
<210> SEQ ID NO 9
<211> LENGTH: 29
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 9
ccacgtgagt tacggctgat cgaccagac                                    29

<210> SEQ ID NO 10
<211> LENGTH: 29
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 10
gcctaggacg tcaactccaa ccgcaccgt                                    29

<210> SEQ ID NO 11
<211> LENGTH: 21
<212> TYPE: DNA
<213> ORGANISM: Agrobacterium rhizogenes

<400> SEQUENCE: 11
acaaggtaga atccgcctga g                                            21

<210> SEQ ID NO 12
<211> LENGTH: 21
<212> TYPE: DNA
<213> ORGANISM: Agrobacterium rhizogenes

<400> SEQUENCE: 12
ttcaactctg gcatctcaga c                                            21

<210> SEQ ID NO 13
<211> LENGTH: 43
<212> TYPE: DNA
<213> ORGANISM: Agrobacterium tumefaciens

<400> SEQUENCE: 13
tcgctttcct tgacgcggag ttcttccaga ccgttcatca cgg                    43

<210> SEQ ID NO 14
<211> LENGTH: 17
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 14
gtaggtgatt ggcgttg                                                 17

<210> SEQ ID NO 15
<211> LENGTH: 44
<212> TYPE: DNA
<213> ORGANISM: Agrobacterium tumefaciens

<400> SEQUENCE: 15
tgaattacgt taagcatgta ataattaaca tgtaatgcat gact                   44
```

```
<210> SEQ ID NO 16
<211> LENGTH: 26
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 16
gttatttatg agatgggttt ttatga                                          26

<210> SEQ ID NO 17
<211> LENGTH: 20
<212> TYPE: DNA
<213> ORGANISM: Escherichia coli

<400> SEQUENCE: 17
aacgcctgat tttacgcgag                                                 20

<210> SEQ ID NO 18
<211> LENGTH: 21
<212> TYPE: DNA
<213> ORGANISM: Escherichia coli

<400> SEQUENCE: 18
caataccgca gggcacttat c                                               21

<210> SEQ ID NO 19
<211> LENGTH: 18
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 19
cccacagatg atgtggac                                                   18

<210> SEQ ID NO 20
<211> LENGTH: 20
<212> TYPE: DNA
<213> ORGANISM: Agrobacterium rhizogenes

<400> SEQUENCE: 20
tggcaaggaa tgggtttgag                                                 20

<210> SEQ ID NO 21
<211> LENGTH: 23
<212> TYPE: DNA
<213> ORGANISM: Agrobacterium rhizogenes

<400> SEQUENCE: 21
ctacaactac aggcgctgct ttt                                             23

<210> SEQ ID NO 22
<211> LENGTH: 15
<212> TYPE: DNA
<213> ORGANISM: Artificial sequence
<220> FEATURE:
<223> OTHER INFORMATION: Description of Artificial Sequence:  Synthetic
      Primer

<400> SEQUENCE: 22
tggcgaagtc tgtcc                                                      15
```

<210> SEQ ID NO 23
<211> LENGTH: 21
<212> TYPE: DNA
<213> ORGANISM: Agrobacterium tumefaciens

<400> SEQUENCE: 23
gccaagggat cttttggaa t                                              21

<210> SEQ ID NO 24
<211> LENGTH: 18
<212> TYPE: DNA
<213> ORGANISM: Agrobacterium tumefaciens

<400> SEQUENCE: 24
ccacccaaac gtcggaaa                                                 18

<210> SEQ ID NO 25
<211> LENGTH: 15
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 25
tgctccgtcg tcagg                                                    15

<210> SEQ ID NO 26
<211> LENGTH: 16
<212> TYPE: DNA
<213> ORGANISM: Agrobacterium tumefaciens

<400> SEQUENCE: 26
gcacccggtg gagctt                                                   16

<210> SEQ ID NO 27
<211> LENGTH: 19
<212> TYPE: DNA
<213> ORGANISM: Agrobacterium tumefaciens

<400> SEQUENCE: 27
tctgcctaac cggctcagt                                                19

<210> SEQ ID NO 28
<211> LENGTH: 19
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 28
catgttggtt tctacgcag                                                19

<210> SEQ ID NO 29
<211> LENGTH: 23
<212> TYPE: DNA
<213> ORGANISM: Solanum tuberosum

<400> SEQUENCE: 29
atgaaataaa aggatgcaca cat                                           23

<210> SEQ ID NO 30
<211> LENGTH: 20
<212> TYPE: DNA

<213> ORGANISM: Solanum tuberosum

<400> SEQUENCE: 30
acaactttga tgcccacatt                                                   20

<210> SEQ ID NO 31
<211> LENGTH: 15
<212> TYPE: DNA
<213> ORGANISM: Artificial sequence
<220> FEATURE:
<223> OTHER INFORMATION: Description of Artificial Sequence: Synthetic
      Primer

<400> SEQUENCE: 31
tgacatgcta atcac                                                        15

<210> SEQ ID NO 32
<211> LENGTH: 1215
<212> TYPE: DNA
<213> ORGANISM: Agrobacterium rhizogenes

<400> SEQUENCE: 32
atggcgaagt ctgtcctaaa agcagcgcct gtagttgtag ggttgacggc cttgatggag        60
cgtcatgccg atgccctctc gagccaactt caagcacatc atcttaaggt tttcccgccg       120
cattccgaga agggcattcg aacattcggg ccatcggagg cgtccaagct gctcggcgtt       180
ggcgagtcat atttacggca gaccgcgtct gagatgccag agttgaatgt tagcatgagc       240
ccgggtggca ggcgaatgtt ctcaattgaa gatatccatg tgattcggaa gtatatggat       300
caggtcggcc gcgggaaccg gcgctacctg ccacatcgtc gaggcggcga gcagcttcag       360
gttatctctg tgatgaattt caaaggtggg tcgggtaaga ccaccaccgc cgcgcatctg       420
gcgcagtacc tcgctatgcg cggatatcga gtcttggcca ttgatctcga tcctcaagcg       480
agcctttctg cactctttgg gagccaaccg gagacggacg ttggcccgaa cgaaacgctc       540
tacggcgcta aaggtatga tgatgagcag gtggcaatcg aacgagtcgt ccgagggact       600
tacattcccg acctccacct gattcctggt aaccttgagc tgatggagtt tgaacacgat       660
acgccacgcg cgctgatgaa ccgcaaagag gcgacacgc tctttatgg tcgcatcagc       720
caagtaattg aagatatcgc ggataactat gacgtcgtgg tcatcgactg ccctcccag       780
cttgggtatc tcacgctatc cgcattgact gcggcgacgt ccattcttgt cacggtccat       840
ccgcagatgc tggatgtgat gtcgatgaac cagtttctgg caatgacatc gaaccttttg       900
cgtgaaatcg agaatgctgg cgccaagttc aagtttaatt ggatgcgcta tctgataacc       960
cgtttcgaac cgagcgacgg accacagaac caaatggtag ttatctgcg gtcgattttt      1020
ggcgaaaatg tcctcaattt tccgatgctt aaaaccaccg cggtttcgga cgctggcctg      1080
acaaaccaga ctctattcga agtggagcgt ggcctgttca cgcgctcgac ctatgatcga      1140
gccttggagg cgatgaacgc cgtcaacgac gagatcgaaa cactgatcaa aaaagcatgg      1200
ggtaggccca catga                                                      1215

<210> SEQ ID NO 33
<211> LENGTH: 939
<212> TYPE: DNA
<213> ORGANISM: Agrobacterium rhizogenes

<400> SEQUENCE: 33
atgccgctcc tcggcgtaac aaggaaggag cgcgatccgg caacgaagct cacagcgaac        60

| | |
|---|---:|
| attggtaacg cactgcgaga gcaaaacgat cgtcttagcc gtgccgaaga gatcgagcgg | 120 |
| cgtctcgctg aaggtcaggc agtgatagag ttggatgcct cgtcaataga accgtctttc | 180 |
| gtgcaggatc gtatgcgagg ggacattgac gggctcctta cttcgatccg ggaacaagga | 240 |
| cagcaagtcc caatccttgt gcgaccgcat ccgagccagc cgggccgata tcaggttgcc | 300 |
| ttcggccacc gccggctacg cgccgtttca gaactcggac ttccggtcag agcggtcgtt | 360 |
| cgcgaactga cggacgagca agtggtcgta gcacagggtc aggaaaacaa tgagcgcgaa | 420 |
| gatcttacct tcatcgaaaa ggcgcgcttc gcacatcgcc tgaacaggca gttttctcga | 480 |
| gagattgtca tcgccgcgat gtcgatcgac aagagcaatt tgtccaagat gcttctgctc | 540 |
| gtcgacgccc tcccctctga actgaccgat gctattggtg ccgctcctgg tgttggacgg | 600 |
| ccgagttggc aacaacttgc cgagctgatt gagaaagttt cttcaccggc cgacgtggct | 660 |
| aaatatgcta tgtcggagga agttcaagcg ctgccatcgg cagaacgatt caaggcggtg | 720 |
| atcgctagtc tgaagcccag tcgggttgcg cgtggacttc ccgaggtcat ggccacccca | 780 |
| gacggcacca gaattgcaca ggtgacgcag agcaaggcca aactggaaat cacgattgac | 840 |
| aggaaggcga cgcccgattt tgcgaccttc gtgctcgatc atgtgccagc gctgtatcaa | 900 |
| gcgtaccacg ctgagaacca acggaaacgg ggagagtaa | 939 |

<210> SEQ ID NO 34
<211> LENGTH: 1218
<212> TYPE: DNA
<213> ORGANISM: Agrobacterium rhizogenes

<400> SEQUENCE: 34

| | |
|---|---:|
| atgatgcaga caggaagtgt aacgacgcca ttcgggcggc ggccaatgac gcttgcgctt | 60 |
| gtgcggcgcc agacggcgct ggccgatatc aaacaaggca agacagcgga caagtggaag | 120 |
| gtctttagag acgcgtccgc ggccatggaa ctacttggaa tccagtccaa cagtcttgcc | 180 |
| gtccttgatg cgctattgag cttthcaccсg gaaacggagt gcgtcagga ggcacagctg | 240 |
| atcgtcttcc cgtcgaatgc tcagcttgcc cttcggcgc atgggatggc tggcgcgact | 300 |
| ttgcgtaggc acatcgccat gctcgtggag tcaggcttga tcgtccggaa ggatagcgcc | 360 |
| aacggaaagc gttacgctcg taaggatggc gctggtcaga tcgagcgcgc gtttggcttc | 420 |
| gatttgtctc cgcttctcgc gcggtccgaa gagctagcga tgatggcaca gcaggtgatg | 480 |
| gccgatcgag cagcattcag gatggccaaa gaaagtctga cgatttgccg acgggacgtt | 540 |
| cggaagctaa ttacggcagc tatggaagag ggagcggagg gcgactggca agctgtcgag | 600 |
| gaagtctatg tggaacttgt gggtagaatt ccacgcgccc cgacgcttgc tgatgtagag | 660 |
| tcaattctcg aagagatgtg gatgctccag gaagagataa tcaaccggtt ggaaattaga | 720 |
| gacaattcag aaaataatag caccaatgct gcccagagcg agcagcacat acagaattca | 780 |
| aaacccgaat ccgttaatga acttgaacct cgctctgaaa aggagcaggg cgctaagccg | 840 |
| agtgaaatag accgggcaag gagcgagccg ataaaagcgt tccccctcgg gatgatcctg | 900 |
| aaagcatgcc cgaccattgg caattatggg ccgagcggtg cggttgctag ctggcgtgac | 960 |
| ctcatgtcgg ctgcggtggt ggttcggtct atgctggggg tcagcccgtc ggcttaccaa | 1020 |
| gacgcgtgtg aggcaatggg accggagaat gcggcagcag cgatggcgtg cattttggag | 1080 |
| cgagcgaact tcatcaattc gcccgggggc tatctccgag atctgacacg gcggagcgag | 1140 |
| ctcgggaagt tttcacttgg cccgatgata atggcgctct tgaaggctag cgggcagggg | 1200 |
| acgttgcggt ttggctag | 1218 |

<210> SEQ ID NO 35
<211> LENGTH: 80
<212> TYPE: DNA
<213> ORGANISM: Agrobacterium rhizogenes

<400> SEQUENCE: 35

| | | |
|---|---|---|
| gccggaagca catccttggc gtctcaactg acgcccctga dacgtcgccc gccgacaata | 60 |
| ggacggcaaa gaaccgctcc | 80 |

<210> SEQ ID NO 36
<211> LENGTH: 152
<212> TYPE: DNA
<213> ORGANISM: Agrobacterium rhizogenes

<400> SEQUENCE: 36

| | | |
|---|---|---|
| accgcaaaag aaaagagccc cctcaacgtc gccgtcgcgg aagcccttct gtctctctag | 60 |
| cgcgaacaga atcgcatttc ctcgaatcct cgtcaagagt ttttagcgcc gttttggtga | 120 |
| gctgatttcc tttgcctgct gaaaggtgaa ag | 152 |

<210> SEQ ID NO 37
<211> LENGTH: 16
<212> TYPE: DNA
<213> ORGANISM: Agrobacterium rhizogenes

<400> SEQUENCE: 37

| | |
|---|---|
| gtggtcagct gaccac | 16 |

<210> SEQ ID NO 38
<211> LENGTH: 1215
<212> TYPE: DNA
<213> ORGANISM: Rhizobium etli

<400> SEQUENCE: 38

| | |
|---|---|
| atgaatatgg caccgcaaat agaaaaagca atttccgatg tcgaccagct gatcatcggt | 60 |
| caggcacagg aactatccga caagctgaag cagcatcgcc tcgaaatgtt tcctccgcgc | 120 |
| gcgctaaagg gtctgcggga atttcagctt gctgaagtgg cgcggtttct cggcgtgacc | 180 |
| agcggctatc ttcgaaatct ttcgctcgag ggcaagggtg ccctccccca ggttacgccg | 240 |
| tctggccgcc gatcgtatac ggcggagcag atggaggaga tgcgtggctt tctcgagcat | 300 |
| aatgcgcgcg ccggaacaca ttatgtgcgt catcgccgcg ccacgaaca tctgcaggtc | 360 |
| gttgctgtcg tcaacttcaa gggggggcagc ggcaagacga cgagtgccgc gcatcttgcc | 420 |
| cagcatctcg ccctgaccgg tcaccgcgtc ctggccgtcg atctcgatcc gcaagcgtct | 480 |
| ctttctgcca tacacggctt tcagccggag ttcgacgtca acgaaaacga dacactctac | 540 |
| gccgccattc gctatgacga tcagcggcgt ccgctgcggg acattatccg gccgaccaac | 600 |
| ttcccgaacc ttcatctcgt gccgggcaat ctcgaactga tggaattcga gcacgatacg | 660 |
| ccgcgggtcc tcgctcaggg caaagcgagc gattatgggc gcgtcttctt tgcccggctg | 720 |
| gatgaggcgc tggcctcggt cgcggatgat tacgacgtcg tcatcatcga ttgcctcccc | 780 |
| cagcttggct ttttgaccat gagcgccatt tgcggtgcga cggcggttct gatcaccgtt | 840 |
| catccgcaga tgctcgatgt catgtcgatg tgccagttcc tgcaaatgct ggcgaagtg | 900 |
| ctgaacacgc tgaagggagc cggcggcaat atgaacctcg actggctgcg ttacctcgtg | 960 |
| acccgctacg atccgcagga cgggccgcag acgcagatgg tcgccttcat gcgctcgatg | 1020 |

-continued

| | |
|---|---|
| ttcaagagcc atgtgctcac caacccgatg ctgcgcagcg tcgcgatctc cgatgcggcg | 1080 |
| atgactaacc agacgctgta cgaagtcgag cgaagtcagt ttacccgcgc gacctatgac | 1140 |
| cgcgccatgg aggcgatgga gtcagtcaac acggaaatcg tcgatctcat ccataaggca | 1200 |
| tggggccgga aatga | 1215 |

<210> SEQ ID NO 39
<211> LENGTH: 1050
<212> TYPE: DNA
<213> ORGANISM: Rhizobium etli

<400> SEQUENCE: 39

| | |
|---|---|
| atggcgcgta aaatcttct gtcgggcctg atggacgatt ccaagaagtt tactgcggta | 60 |
| aacaatgagg atgagccggc ccctcgcgac gagaggcagc atatcaccta taagggggatt | 120 |
| ggcgcgctcg gtgcggtcac ccgcagcatc gatgccttgg ccgccaaggc cgatgccgcc | 180 |
| aaggcgatcg aagagcagct ggcgagcggc gagacggtga tcgatctcga cccggcgctg | 240 |
| atcgaagatt ccttcgtgac cgaccggctg gcgcatactg acgaacagtt ccgggaatta | 300 |
| gtcgaggcga tccgcctgcg cggccaggat tcaccgatcc ttgtgcgccc gcatcccgag | 360 |
| agggaggggc gatatcagat cgcttttggt catcgtcgtg cgcgggcggc aaaggagctc | 420 |
| ggccgacctg tccgggcggt ggtcaagaga ctcgacgacc gcgaccatgt cattgcgcag | 480 |
| ggccaggaga attcggcacg cgccgatctc tccttcatcg agaggacgat gtttgccgac | 540 |
| aagctcgaca cgttgggttt cgaccgggaa acgatcatgt cggcactcag cgcagacaag | 600 |
| acgacggtgt ccaagatgct gtcggtcacg aagcggattc cggccgaagt cctggccgcg | 660 |
| atcggcgtag ccaagacgac tggccgcgat cgctggcatg atctttcggc gaaattcgag | 720 |
| acggaaaaca tcgcagcccg ggcgattgag ttcaccagat cggtggagtt cgagacggcc | 780 |
| gagccggacg cccgcttcga catgcttgtc gccttcatca gcaggaacca acaggcgtcg | 840 |
| cccgccgccg cagttcagcc cgtggcgcac gcctggcagc gccgggacgg agccgtcaaa | 900 |
| gcgaagatca aggatgatgg aaaacagttc accatcgcgc tgaaggcgga aaggcatct | 960 |
| gcctttggcg cctacatcgc cagcaatctg gatcgtctct acgaggcgtt cgagaagaca | 1020 |
| caggatttga cgaagaacgg agatcaataa | 1050 |

<210> SEQ ID NO 40
<211> LENGTH: 1293
<212> TYPE: DNA
<213> ORGANISM: Rhizobium etli

<400> SEQUENCE: 40

| | |
|---|---|
| atggaaagcg gaagtgtgac gacgcccttc gggcggcggc cgatgacgtt tggcatgttg | 60 |
| gcaagtcagg ccgctgcccg aaaaatcgag cccggccgat cgattgataa atggaaactc | 120 |
| tatcgcgccc tgtgcgaggc caggccgctg ctcggcatta cagaccgggc gctttccatc | 180 |
| ctgaacgcct tgctgagctt ttatcccaag ggagagctct ccgaggagaa cggcttggtc | 240 |
| gtatttcctt cgaatacgca gctctctctg cgcgcgcatg aatggcgga gcagacgatc | 300 |
| cgtcgccacc tggcggcgct gatcgaggcc ggattgctga tccgcaagga cagcccgaac | 360 |
| ggcaagcgtt acgctcgcaa ggagcagggc ggggagatcc gtgaggcatt cggcttctcg | 420 |
| ctggccgcgc tgcttgcgcg cgcggacgag atcgagcggc tggcggccga gatggcagcc | 480 |
| gaacgattgc agctgcagcg gctcaaagag cgcctgacgc tttgcaggcg cgacatcgcc | 540 |
| aagctcatcg agatggccgt ggaagagggc gcctctggtg attggagcgg ggtccacctg | 600 |

```
catttttcgag gcatcgtcga acggctgccg cgctcgccat ccttcgagaa gattgccgcc    660
gcactcgacg aactggaact gttgcgcgaa gaaatcacca atcagttgga aatgcaggtt    720
aaagctccaa atcaaagcgg caatgcccaa cattctgagc ggcacataca gaattcaaac    780
ccacactaca ctactgaact tgaaccacgc ttcgaaacga agcagggcgc aacggtggac    840
gaccaatcgg aaggttgggc cgagccgagg gccagaatag cgacacagga ggggaagggc    900
aggcccatgc cagctgcaaa ctcagcctcg gttgccggcg gcgggctcaa atccttcccg    960
ctgggcctgg tgctgcaggc ctgcccagag atcgccgcct atggaccgca gggctcggtg   1020
ggcacatggc gcgatctgat ggcggcggct gtcgtcgtgc gctcaatgct cggagtgagc   1080
ccctcggcct atgaacaggc ctgcgaggtc atggggcctg aaaatgcggc taccgtcata   1140
gcgtgcgtgc ttgaaagggc agggcacatc aattccgccg gtggttacct ccgtgacctg   1200
acccgccgcg ccgagagagg cgaatttgcc atcggaccga tgttgatggc gcttgtccgc   1260
accaattcgc caatcagagg caagaccgga tga                                1293
```

```
<210> SEQ ID NO 41
<211> LENGTH: 42
<212> TYPE: DNA
<213> ORGANISM: Rhizobium etli

<400> SEQUENCE: 41
gcgggaagtt tactgcggta aaccggggca aggagctggt tg                       42

<210> SEQ ID NO 42
<211> LENGTH: 149
<212> TYPE: DNA
<213> ORGANISM: Rhizobium etli

<400> SEQUENCE: 42
gcaaaagaaa aggcccccga acgttgccgt cgcggaagcc ctctctgatc tagacaccca    60
gagaatcaca tttccgcgaa tcatagtcaa gagtctttgg caccgaattt ggtgaggcgt   120
gatcttttgc cttgaagaag gcgaagaaa                                      149

<210> SEQ ID NO 43
<211> LENGTH: 331
<212> TYPE: DNA
<213> ORGANISM: Agrobacterium tumefaciens

<400> SEQUENCE: 43
aggatttttc ggcgctgcgc tacgtccgcg accgcgttga gggatcaagc cacagcagcc    60
cactcgacct tctagccgac ccagacgagc caagggatct ttttggaatg ctgctccgtc   120
gtcaggcttt ccgacgtttg ggtggttgaa cagaagtcat tatcgcacgg aatgccaagc   180
actcccgagg ggaaccctgt ggttggcatg cacatacaaa tggacgaacg gataaacctt   240 ttcacgcccct tttaaatatc cgattattct aataaacgct cttttctctt aggtttaccc   300
gccaatatat cctgtcaaac actgatagtt t                                   331

<210> SEQ ID NO 44
<211> LENGTH: 442
<212> TYPE: DNA
<213> ORGANISM: Agrobacterium tumefaciens

<400> SEQUENCE: 44
ctcatctaag cccccatttg gacgtgaatg tagacacgtc gaaataaaga tttccgaatt    60
```

-continued

```
agaataattt gtttattgct ttcgcctata aatacgacgg atcgtaattt gtcgttttat    120
caaaatgtac tttcatttta taataacgct gcggacatct acatttttga attgaaaaaa    180
aattggtaat tactctttct ttttctccat attgaccatc atactcattg ctgatccatg    240
tagatttccc ggacatgaag ccatttacaa ttgaatatat cctgccgccg ctgccgcttt    300
gcacccggtg gagcttgcat gttggtttct acgcagaact gagccggtta ggcagataat    360
ttccattgag aactgagcca tgtgcacctt cccccaaca cggtgagcga cggggcaacg    420
gagtgatcca catgggactt tt                                             442
```

VECTORS AND METHODS FOR IMPROVED PLANT TRANSFORMATION EFFICIENCY

This application is a divisional of U.S. application Ser. No. 11/516,036, filed Sep. 5, 2006, which issued as U.S. Pat. No. 8,993,846 on Mar. 31, 2015, which claims the priority of U.S. provisional application Ser. No. 60/714,501, filed Sep. 6, 2005, each of the entire contents of which are incorporated by reference herein.

BACKGROUND OF THE INVENTION

1. Field of the Invention

The invention relates generally to the field of molecular biology. More specifically, the invention relates to improved methods for plant genetic transformation and compositions for achieving the same.

2. Description of Related Art

Transformation of plant cells by an *Agrobacterium*-mediated method involves exposing plant cells and tissues to a suspension of *Agrobacterium* cells that contain certain DNA plasmids. These plasmids have been specifically constructed to contain transgenes that will express in plant cells (see, for example, U.S. Pat. No. 5,034,322). Most often, one or more of the transgenes is a positive selectable marker transgene that permits plant cells to grow in the presence of a positive selection compound, such as an antibiotic or herbicide. These cells can be further manipulated to regenerate into whole fertile plants.

The methods for introducing transgenes into plants by an *Agrobacterium*-mediated transformation method generally involve a T-DNA (transfer DNA) that incorporates the genetic elements of at least one transgene and transfers those genetic elements into the genome of a plant. The transgene(s) are typically constructed in a DNA plasmid vector and are usually flanked by an *Agrobacterium* Ti plasmid right border DNA region (RB) and a left border DNA region (LB). During the process of *Agrobacterium*-mediated transformation, the DNA plasmid is nicked by an endonuclease, VirD2, at the right and left border regions. A single strand of DNA from between the nicks, called the T-strand, is transferred from the *Agrobacterium* cell to the plant cell. The sequence corresponding to the T-DNA region is inserted into the plant genome.

The integration of the T-DNA into the plant genome generally begins at the RB and continues to the end of the T-DNA, at the LB. However, the endonucleases sometimes do not nick equally at both borders. When this happens, the T-DNA that is inserted into the plant genome often contains some or all of the plasmid vector DNA. This phenomenon is referred to as "border read-through." It is usually preferred that only the transgene(s) located between the right and left border regions (the T-DNA) is transferred into the plant genome without any of the adjacent plasmid vector DNA (the vector backbone). The vector backbone DNA contains various plasmid maintenance elements, including for example, origin of replications, bacterial selectable marker genes, and other DNA fragments that are not required to express the desired trait(s) in commercial crop products.

Considerable resources are directed at screening the genome of transgenic crop plants for the presence the vector backbone DNA. Methods such as polymerase chain reaction (PCR) and Southern blot analysis are most often employed to identify the extraneous vector backbone DNA. These methods are time consuming and expensive for large-scale screening work. The transgenic plants that are found to contain vector backbone DNA are generally not preferred for commercialization. Further, transgenic plants containing more than two transgenes are usually of little value for commercial development. Substantial efforts are expended regenerating plants from plant cell culture that have no commercial potential.

Thus, it would be of great benefit if methods and compositions could be developed that would greatly reduce the occurrence of vector backbone DNA in the genome of transgenic plants and/or increase the frequency of low copy transformation events. Fewer transgenic plants would have to be produced if a greater number were free from vector backbone DNA and most plants have one or two copies of the transgenes, greatly increasing the efficiency of transgenic plant production.

SUMMARY OF THE INVENTION

In accordance with one aspect of the invention, constructs and methods are provided for improving the quality of events in bacterially-mediated plant cell transformation, such as *Agrobacterium*-mediated plant transformation. The invention is advantageous in providing a reduced frequency of vector backbone DNA, i.e., non-T-DNA region, transformation events and of increasing the frequency of T-DNA transformation events with one or two copies of the T-DNA.

The invention also provides DNA constructs for transforming plants comprising: i) at least one T-DNA border region; ii) at least one heterologous transgene adjacent to the border region; iii) a coding region for a bacterial selectable marker; and iv) at least one segment of DNA, comprising a cis and/or trans element or elements of a replication origin for maintaining a low copy number of the DNA construct in a plant cell transforming bacterium.

In certain embodiments of the invention, the elements of the replication origin for maintaining low copy number of a DNA construct in a plant cell transforming (plant cell transformation competent) bacterial cell comprise one or more of repA (e.g. SEQ ID NO:32 or SEQ ID NO:38); repB (e.g. SEQ ID NO:33 or SEQ ID NO:39); repC (e.g. SEQ ID NO:34 or SEQ ID NO:40); igs1 (e.g. SEQ ID NO:35 or SEQ ID NO:41); igs2 (e.g. SEQ ID NO:36 or SEQ ID NO:42). A construct may also optionally include a palindromic sequence, for example, the 16 bp palindromic sequence of SEQ ID NO:37. These elements may be arranged in cis or in trans with respect to each other.

In some embodiments, the a T-DNA border region is defined as a right border region (RB) or a left border (LB) region. Further, in certain embodiments the RB and/or LB sequences comprise SEQ ID NO:43 or SEQ ID NO:44. In particular embodiments, a heterologous transgene when expressed in a transformed plant cell provides an agronomic phenotype to the cell or transformed plant derived from the cell. In further embodiments, a coding region for a bacterial selectable marker is an antibiotic resistance gene selected from kanamycin resistance gene, gentamycin resistance gene, chloramphenicol resistance gene, spectinomycin resistance gene, streptomycin resistance gene, tetracycline resistance gene, ampicillin resistance gene, blasticidin resistance gene, hygromycin resistance gene, puromycin resistance gene, or Zeocin resistance gene.

In some embodiments, a replication origin comprises a repABC sequence selected from SEQ ID NOs: 1, 2, 3, or 4. In one embodiment, the at least one segment of DNA comprises replication genes repA, repB, and repC. In some embodiments, the at least one segment of DNA comprises intergenic sequence 1 (igs1) and intergenic sequence 2 (igs2). In some embodiments, the at least one segment of DNA comprises a 16 base pair palindromic sequence. In other embodiments the segment of DNA comprises all sequences of repABC necessary for maintaining low copy number (1-3 copies per cell) in *Agrobacterium* or other plant cell transforming competent bacteria. Constructs containing repABC and methods or their use are described in more detail below.

The DNA constructs of the present invention may be transferred to any cell, for example, such as a plant cell transformation competent bacterium. Such bacteria are known in the art and may, for instance, belong to the following species: *Agrobacterium* spp., *Rhizobium* spp., *Sinorhizobium* spp., *Mesorhizobium* spp., *Phyllobacterium* spp. *Ochrobactrum* spp. and *Bradyrhizobium* spp. Preferably, such bacteria may belong to *Agrobacterium* spp. The DNA constructs of the present invention may further comprise one or more replication origins for maintaining copies of the construct in *E. coli*. In some embodiments, origin of replication for maintaining copies of the construct in *E. coli* is derived from at least one of pBR322 and pUC.

The present invention also relates to a plant cell transforming bacterium comprising the DNA construct of the present invention, and which may be used for transforming a plant cell. In some embodiments, the plant transforming bacteria is selected from *Agrobacterium* spp., *Rhizobium* spp., *Sinorhizobium* spp., *Mesorhizobium* spp., *Phyllobacterium* spp. *Ochrobactrum* spp. or *Bradyrhizobium* spp.

The present invention also relates to a method for transforming a plant cell comprising: contacting at least a first plant cell with a plant cell transforming bacteria of the present invention; and selecting at least a plant cell transformed with at least one heterologous transgene. In some embodiments, the plant cell is a soybean, canola, corn, or cotton plant cell. In one embodiment, a method of the invention further comprises regenerating a plant from the plant cell.

The present invention also relates to a method of producing food, feed or an industrial product comprising: obtaining the plant of the present invention or a part thereof; and preparing the food, feed or industrial product from the plant or part thereof.

The invention also includes methods of genetically transforming plants with the DNA constructs of the present invention and reducing the frequency of plants transformed with non-T DNA vector region In some embodiments, the frequency of plants transformed with non-T-DNA region may be defined as less than or equal to about 20%. In some embodiments, the frequency is less than or equal to about 15%, in some embodiments less than about 10%, and in some embodiments less than or equal to about 8% or 5%. In some embodiments of the methods of the invention, the frequency of one- or two-copy T-DNA transformation events obtained is greater than or equal to about 70% or 75%. In some instances, that frequency can be raised to greater than or equal to about 80% or 85%, and in some embodiments, to greater than about 90% or 95%.

In addition to a full length oriRi, the present invention encompasses plant transformation vectors containing mutants and variants of oriRi that retain substantially similar function to the full length sequence when used in the present invention. For example, applicants have identified the truncated sequence disclosed in SEQ ID NO: 3 that is suitable for use in the present invention. One of skill in the art can readily make additional changes, deletions, substitutions, etc in the oriRi sequence and screen for functional activity using the methods of the present invention. Thus, the present invention encompasses such variants and mutants.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate different embodiments of the invention and together with the description, serve to explain the principles of the invention.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

DETAILED DESCRIPTION OF THE INVENTION

Figure 1:
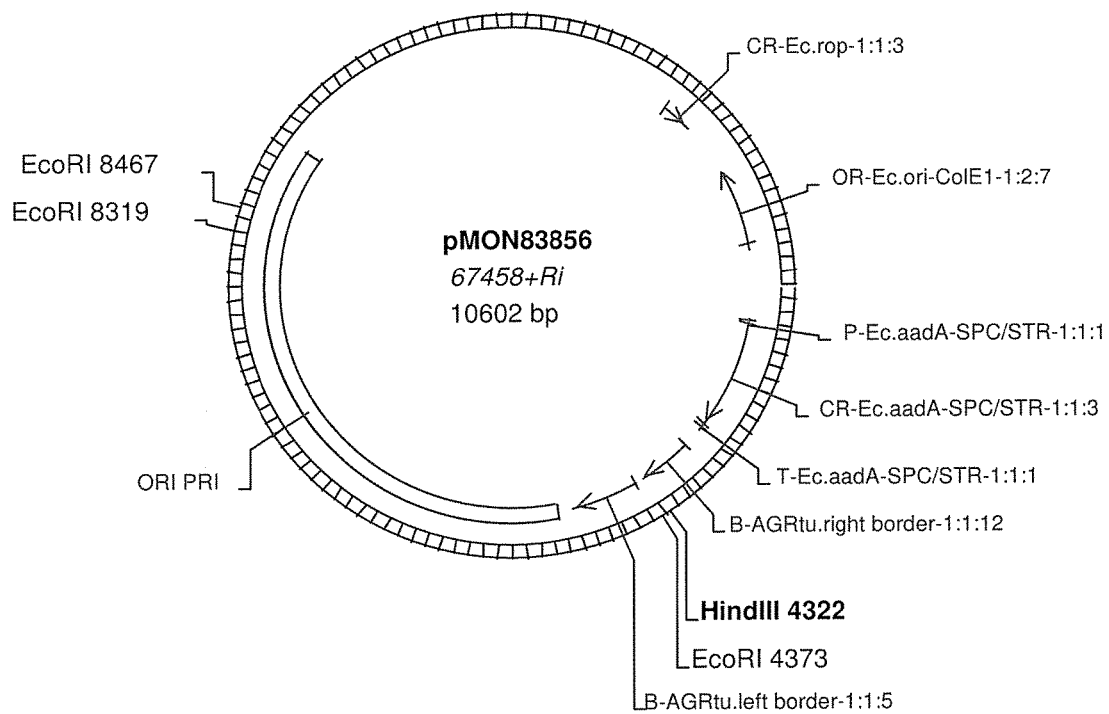
FIG. 1 shows a plasmid map of pMON83856, the base vector with a 5.6 kb oriRi fragment used for construction of pMON83882 for soybean transformation and pMON97352 for corn transformation.

The invention will now be described by reference to more detailed embodiments, with occasional reference to the accompanying drawings. This invention may, however, be embodied in different forms and should not be construed as limited to the embodiments set forth herein. Rather, these embodiments are illustrative and provided so that this disclosure will be thorough and complete, and will fully convey the scope of the invention to those skilled in the art.

The present invention relates, in part, to the discovery that the repABC origin of replication, such as the one from *Agrobacterium rhizogenes* pRi ("oriRi" or "oriPRi"), which maintains 1-3 copies in bacteria such as *Agrobacterium*, can be used in plant transformation vectors and can impart highly desirable transformation events. The vectors of the invention can, for example, significantly reduce the frequency of transformation events that transfer non-T-DNA region, i.e., vector backbone DNA, and can, for example, significantly increase the number of one- or two-copy T-DNA, i.e., the gene of interest, transformation events. The prior art does not teach or suggest the use of oriRi to achieve these unexpected transformation results. The vectors and methods of the invention improve transformation events in the preparation of transgenic crop plants.

As used herein, a transgenic crop plant contains an exogenous polynucleotide molecule or a heterologous transgene inserted into the genome of a crop plant cell. A crop plant cell, includes without limitation, a plant cell, and further comprises suspension cultures, embryos, meristematic regions, callus tissue, leaves, roots, shoots, gametophytes, sporophytes, ovules, pollen and microspores, and seeds, and fruit. By "exogenous" or "heterologous" it is meant that a polynucleotide molecule which originates from outside the plant cell into which the polynucleotide molecule is introduced. An exogenous polynucleotide molecule can have a naturally occurring or non-naturally occurring nucleotide sequence. One skilled in the art understands that an exogenous polynucleotide molecule can be a heterologous molecule derived from a different species of any other organism or the plant species than the plant into which the polynucleotide molecule is introduced or can be a polynucleotide molecule derived from the same plant species as the plant into which it is introduced.

The exogenous polynucleotide (heterologous transgene) when expressed in a transformed plant cell provides an agronomic trait to the cell or to a transformed plant derived from the cell. These genes of interest (GOI) provide beneficial agronomic traits to crop plants, for example, including, but not limited to genetic elements comprising herbicide resistance (U.S. Pat. No. 5,633,435; U.S. Pat. No. 5,463,175), increased yield (U.S. Pat. No. 5,716,837), insect control (U.S. Pat. No. 6,063,597; U.S. Pat. No. 6,063,756; U.S. Pat. No. 6,093,695; U.S. Pat. No. 5,942,664; U.S. Pat. No. 6,110,464), fungal disease resistance (U.S. Pat. No. 5,516,671; U.S. Pat. No. 5,773,696; U.S. Pat. No. 6,121,436; and U.S. Pat. No. 6,316,407; and U.S. Pat. No. 6,506,962), virus resistance (U.S. Pat. No. 5,304,730 and U.S. Pat. No. 6,013,864), nematode resistance (U.S. Pat. No. 6,228,992), bacterial disease resistance (U.S. Pat. No. 5,516,671), starch production (U.S. Pat. No. 5,750,876 and U.S. Pat. No. 6,476,295), modified oils production (U.S. Pat. No. 6,444,876), high oil production (U.S. Pat. No. 5,608,149 and U.S. Pat. No. 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. No. 5,985,605 and U.S. Pat. No. 6,171,640), biopolymers (U.S. Pat. No. 5,958,745 and U.S. Patent Pub 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

The present invention provides plant recombinant DNA constructs for producing transgenic crop plants. Methods that are well known to those skilled in the art may be used to prepare the crop plant recombinant DNA construct of the present invention. These methods include in vitro recombinant DNA techniques, synthetic techniques, and in vivo genetic recombination. Such techniques are described in Sambrook et al. (1989). Exogenous polynucleotide molecules created by the methods may be transferred into a crop plant cell by a plant transforming bacterium such as *Agrobacterium* or by other methods known to those skilled in the art of plant transformation. Gene transfer to plants has been shown using diverse species of bacteria as described in Broothaerts et al. (2005) and the U.S. provisional application 60/800,872, herein incorporated by reference. The recombinant DNA constructs of the present invention may be transferred into a crop plant cell by transformation using *Sinorhizobium meliloti*, *Rhizobium* sp., *Mesorhizobium loti*, or any other bacterium capable of transforming a plant cell.

The invention includes plant transformation vectors for use in *Agrobacterium*-mediated transformation of plants. The vectors of the present invention are generally plasmids, but the oriRi replication origin may be replaced by other replication origins from the repABC family for maintaining very low copy number (1-3 copies per cell) in *Agrobacterium*. Also, vectors without an *Agrobacterium*-maintaining replication origin are capable of maintaining themselves in *Agrobacterium* with sequences in the T-DNA that can be integrated into either the Ti plasmid in *A. tumefaciens*, Ri plasmid in *A. rhizogenes* or *Agrobacterium* chromosome through homologous recombination. This results in the same effect of a reduction in non T-DNA sequence insertion and an increase in low copy number transformation events, since the chromosome, Ti or Ri plasmid is present in a single copy. When *Rhizobia* or non *Agrobacterium* species are used for plant transformation, T-DNA containing GOI can be integrated into the chromosome or into repABC plasmids in the host bacteria, which can produce the same effect as *Agrobacterium* does.

A vector of the present invention may comprise at least one of *Agrobacterium* Ti plasmid right border or left border region. The vectors may comprise at least one pair of borders. The vectors can include four pairs of borders, but the vector often comprise one or two pairs.

The vectors of the present invention may further comprise a coding region for a selectable marker for the maintenance in bacterial hosts. Coding regions for selectable markers include Spec/Strp that encodes for Tn7 aminoglycoside adenyltransferase (aadA) conferring resistance to spectinomycin or streptomycin, or a gentamycin (Gm, Gent) selectable marker gene. Other resistance genes include carbenecillin, ampicillin, and kanamycin resistance genes. Others are known and may be readily used in the present invention by those of skill in the art.

The vectors of the present invention may also comprise a coding region for a plant selectable marker gene, which is typically located in T-DNA, to select transformed plant cells with the corresponding reagent. The plant selectable marker may provide resistance to a positive selection compound, for example, antibiotic resistance (e.g., kanamycin, G418, bleomycin, hygromycin, etc.), or herbicide resistance (e.g., including but not limited to: glyphosate, Dicamba, glufosinate, sulfonylureas, imidazolinones, bromoxynil, dalapon, cyclohexanedione, protoporphyrinogen oxidase inhibitors, and isoxaflutole herbicides). Polynucleotide molecules encoding proteins involved in herbicide tolerance are known in the art, and include, but are not limited to a polynucleotide molecule encoding a) tolerance to a glyphosate include 5-enolpyruvylshikimate-3-phosphate synthases (EPSPS; U.S. Pat. No. 5,627,061, U.S. Pat. No. 5,633,435, U.S. Pat. No. 6,040,497, U.S. Pat. No. 5,094,945, WO04074443, and WO04009761), glyphosate oxidoreductase (GOX; U.S. Pat. No. 5,463,175), glyphosate decarboxylase (WO05003362 and U.S. Patent Application 20040177399), and glyphosate-N-acetyl transferase (GAT; U.S. Patent publication 20030083480) conferring tolerance to glyphosate; b) dicamba monooxygenase (DMO, encoded by ddmC) conferring tolerance to auxin-like herbicides such as dicamba (U.S. Patent Applications 20030115626, 20030135879; Herman et al., 2005); c) phosphinothricin acetyltransferase (bar) conferring tolerance to phosphinothricin or glufosinate (U.S. Pat. No. 5,646,024, U.S. Pat. No. 5,561,236, EP 275,957; U.S. Pat. No. 5,276,268; U.S. Pat. No. 5,637,489; U.S. Pat. No. 5,273,894); d) 2,2-dichloropropionic acid dehalogenase conferring tolerance to 2,2-dichloropropionic acid (Dalapon) (WO9927116); e) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105; U.S. Pat. No. 5,767,366, U.S. Pat. No. 4,761,373; U.S. Pat. No. 5,633,437; U.S. Pat. No. 6,613,963; U.S. Pat. No. 5,013,659; U.S. Pat. No. 5,141,870; U.S. Pat. No. 5,378,824; U.S. Pat. No. 5,605,011); f) haloarylnitrilase (Bxn) for conferring tolerance to bromoxynil (WO8704181A1; U.S. Pat. No. 4,810,648; WO8900193A); g) modified acetyl-coenzyme A carboxylase for conferring tolerance to cyclohexanedione (sethoxydim) and aryloxyphenoxypropionate (haloxyfop) (U.S. Pat. No. 6,414,222); h) dihydropteroate synthase (sulI) for conferring tolerance to sulfonamide herbicides (U.S. Pat. No. 5,597,717; U.S. Pat. No. 5,633,444; U.S. Pat. No. 5,719,046); i) 32 kD photosystem II polypeptide (psbA) for conferring tolerance to triazine herbicides (Hirschberg et al., 1983); j) anthranilate synthase for conferring tolerance to 5-methyltryptophan (U.S. Pat. No. 4,581,847); k) dihydrodipicolinic acid synthase (dapA) for conferring to tolerance to aminoethyl cysteine (WO8911789); l) phytoene desaturase (crtI) for conferring tolerance to pyridazinone herbicides such as norflurazon (JP06343473); m) hydroxy-phenyl pyruvate dioxygenase for conferring tolerance to cyclopropylisoxazole herbicides such as isoxaflutole (WO 9638567; U.S. Pat. No. 6,268,549); n) modified protoporphyrinogen oxidase I (protox) for conferring tolerance to protoporphyrinogen oxidase inhibitors (U.S. Pat. No. 5,939,602); and o) aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

In addition to a plant selectable marker, in some embodiments it may be desirable to use a reporter gene. In some instances, a reporter gene may be used with or without a selectable marker. Reporter genes are genes that are typically not present in the recipient organism or tissue and typically encode for proteins resulting in some phenotypic change or enzymatic property. Examples of such genes are provided in Wising et al. (1988), that is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al. (1987) to identify transformed cells, referred to herein as GUS.

In some embodiments, the vectors of the present invention comprise one replication origin for maintenance in *E. coli*. These origins of replication may be derived, for example, from pBR322 or from pUC. One example of such an origin of replication is ColE1. The vectors of the present invention can include any origin of replication which maintains at least 2, 3, 4, 5, 6, 7, 8, 9, 10, 15, 20, 25, 30, 35, 40, 45, 50, 60, 70, 80, 90, or 100 or more plasmid copies in *E. coli*. In some embodiments, the ori maintains a higher copy number in *E. coli* (e.g., greater than 5, 10, 15, 20, 25, or 30, and in some further embodiments, greater than 10, 15, 20, 25 or 30). Such high copy number vectors make it easier to amplify the amount of DNA available for transformation. Thus, in some embodiments, the present invention includes a vector containing an on that provides high copy numbers in *E. coli* cells, and a second ori, such as an ori belonging to the repABC family, for example, oriRi, that maintains extremely low copy number, for example 1-3, in *Agrobacterium*.

The vectors of the present invention also comprise at least one segment of DNA, comprising cis and/or trans elements, which is necessary and sufficient for low-copy plasmid maintenance (1-3 copies) in a plant transforming bacterium such as *Agrobacterium*. The at least one segment of DNA preferably comprises an origin of replication from the repABC family. Further, the at least one segment of DNA may include a Ri plasmid replication origin of *Agrobacte*-

*rium rhizogenes* (oriRi) and/or repABC origin from plasmid p42b of *Rhizobium etli*. Still further, the repABC family preferably comprises replication genes repA, repB, and repC. The at least one segment also may comprise intergenic region sequences, igs1 and igs2. Still further, the at least one segment of DNA may include a 16-bp palindrome after repC.

As used herein, the "origin of replication" of a "repABC" plasmid, i.e. a plasmid that utilizes such sequences for replication and partitioning in a cell, may be defined as comprising repA (e.g. SEQ ID NO:32 from pRi of *A. rhizogenes*; SEQ ID NO:38 from p42b of *R. etli*), repB (e.g. SEQ ID NO: SEQ ID NO:33 from *A. rhizogenes*; SEQ ID NO:39 from p42b of *R. etli*), repC (e.g. SEQ ID NO: SEQ ID NO:34 from *A. rhizogenes*; SEQ ID NO:40 from p42b of *R. etli*), igs1 (e.g. SEQ ID NO:35 from *A. rhizogenes*; SEQ ID NO:41 from p42b of *R. etli*)), igs2 (e.g. SEQ ID NO:36 from *A. rhizogenes*; SEQ ID NO:42 from p42b of *R. etli*), and may optionally comprise a palindromic sequence (e.g. SEQ ID NO:37). In other embodiments, the origin of replication may comprise those sequences required for maintaining low copy number (for example, from 1 to about 3 copies) within a plant-cell-transforming bacterial cell. Examples of such repABC origins of replication are found in SEQ ID NOs:1-4, in the oriRi of the Ri plasmid of *A. rhizogenes*, and in plasmid p42b of *R. etli*, among others.

In one embodiment, the at least one segment is as identified in SEQ ID NO:1. In other embodiments, the at least one segment consists essentially of the following sequence: 5618 bp oriRi of pMON83882 bases (633-6250) identified as SEQ ID NO:2. In another embodiment, the at least one segment comprises and/or consists essentially of the sequence identified in SEQ ID NO:3. In yet another embodiment, the at least one segment may be repABC from p42b from *R. etli* as identified in SEQ ID NO:4.

Encompassed within the definition of any of the nucleic acid or polypeptide sequence defined herein are sequences which exhibit a specified degree of identity to such sequences. For example, it should be noted that while specific nucleic acid sequences are set forth herein, modifications may be made to the described sequences without departing from the scope of the invention. In particular, nucleic acid sequences which are substantially identical to those set forth herein may be used with the present invention. A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85%, 86%, 87%, 88%, or 89% identity, and most preferably at least about 90%, 91%, 92%, 93%, 94%, 95%, 96%, 97%, 98%, or 99% identity over a comparison window of at least 200 nucleotide positions, preferably at least 300 nucleotide positions, more preferably at least 400 nucleotide positions, and most preferably over the entire length of the first nucleic acid. Optimal alignment of sequences for aligning a comparison window may be conducted by the similarity method of Pearson and Lipman (1988); preferably by computerized implementations of these algorithms in the Wisconsin Genetics Software Package Release 7.0, Genetics Computer Group, Madison, Wis. The reference nucleic acid may be a full-length molecule or a portion of a longer molecule.

Alternatively, two nucleic acids have substantial identity if one hybridizes to the other under stringent hybridization conditions. The term "stringent hybridization conditions" is defined as conditions under which a test sequence hybridizes specifically with a target sequence(s) but not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure (see for example Sambrook et al., 1989, at 9.52-9.55, Sambrook et al., 1989 at 9.47-9.52, 9.56-9.58; Kanehisa, 1984; and Wetmur and Davidson, 1968). Appropriate stringent conditions for DNA hybridization are, for example, 6.0× sodium chloride/sodium citrate (SSC) at about 45° C., followed by a wash of 0.2×SSC at 50° C. Details of such methods are known to those skilled in the art or can be found in laboratory manuals including but not limited to Current Protocols in Molecular Biology (1989). In some embodiments, lower stringency conditions may be used by changing the wash to about 2.0×SSC at 50° C. In addition, the temperature in the wash step can be increased from low stringency conditions at room temperature, about 22° C., to higher stringency conditions at about 65° C. Both temperature and salt may be varied, or either the temperature or the salt concentration may be held constant while the other variable is changed. For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" is they can hybridize to one another with sufficient stability to permit them to remain annealed to one another under conventional "high stringency" conditions. It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results. Conventional stringency conditions are described in Sambrook, et al. (1989) and by Haymes et al. (1985).

The DNA construct of the present invention may be introduced into the genome of a desired plant host by a suitable *Agrobacterium*-mediated plant transformation method. Methods for transforming plants by *Agrobacterium tumefaciens*-mediated transformation include: Fraley et al., (1985), and Rogers et al., (1987). *Agrobacterium*-mediated transformation is achieved through the use of a genetically engineered soil bacterium belonging to the genus *Agrobacterium*. Several *Agrobacterium* species mediate the transfer of a specific DNA known as "T-DNA," that can be genetically engineered to carry any desired piece of DNA into many plant species. The major events marking the process of T-DNA mediated pathogenesis are induction of virulence genes, and processing and transfer of the T-strand. This process is the subject of many reviews (Ream, 1989; Howard and Citovsky, 1990; Kado, 1991; Winans, 1992; Zambryski, 1992; Gelvin, 1993; Binns and Howitz, 1994; Hooykaas and Beijersbergen, 1994; Lessl and Lanka, 1994; Zupan and Zambryski, 1995). Non-*Agrobacterium* species such as *Sinorhizobium meliloti, Rhizobium* sp., *Mesorhizobium loti*, may also be used for transferring genes using the DNA constructs of the present invention (Broothaerts et al., 2005 and the U.S. provisional application 60/800,872, herein incorporated by reference). Other methods for introducing DNA into cells may also be used. These methods are well known to those of skill in the art and can include to chemical methods and physical methods such as microinjection, electroporation, and micro-projectile bombardment.

Plant cell regeneration techniques rely on manipulation of certain phytohormones in a tissue culture growth medium, also typically relying on a biocide and/or herbicide marker that has been introduced together with the desired nucleotide sequences. Choice of methodology with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al. (1984); Shimamoto et al. (1989); Fromm (1990); Vasil et al., (1990); Vasil et al. (1992); Hayashimoto (1990); and Datta et al. (1990). Such regeneration techniques are described generally in Klee et al. (1987). Methods and compositions for transforming plants by introducing a transgenic DNA construct into a plant genome in the practice of this invention can include any of the well-known and demonstrated methods. For example, *Agrobacterium*-mediated transformation as illustrated in U.S. Pat. Nos. 5,824,877; 5,591,616; and 6,384,301, all of which are incorporated herein by reference.

Plants that can be made by practice of the present invention include any plants that are subject to transformation and regeneration and include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, Chinese cabbage, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini. In preferred embodiments, the plant is a soybean, corn, canola, or cotton plant. In particular embodiments, the plant is a corn plant. In particular embodiments, the plant is a soybean plant. In other embodiments, the plant is a cotton plant. And in still further embodiments, the plant is a canola plant.

The present methods yield improved transformation efficiencies, significantly reducing the frequency of plants transformed with vector backbone DNA, or "non-T-DNA." In some embodiments, the frequency of plants transformed with non-T DNA is less than or equal to about 20%. In some embodiments, the frequency of plants transformed with non-T DNA is less than or equal to about 15%, or less than equal to about 10%, or less than or equal to about 8% or 5%. Additionally, the methods of the invention yield very high one- or two-copy T-DNA transformation events. For example, in some embodiments, the frequency of one- or two-copy T-DNA transformation events is greater than or equal to about 70% or 75%, as measured using Southern blotting. In some embodiments, that frequency is greater than or equal to about 80% or 85%, and in some cases, 90% or 95%, as measured with Southern blotting.

In some embodiments, the frequency of plants transformed with non-T DNA vector region is about 50%, 40%, 20%, 15%, or 10% lower than the frequency of T-DNA found in the same variety of plant that has been transformed with a plant transformation vector that does not contain the repABC element such as oriRi element of the present invention. In other embodiments, the frequency of one- or two-copy T-DNA transformation events is about 50%, 40%, 20%, 15%, or 10% higher than the frequency of one- or two-copy T-DNA transformation events relative to the same variety of plant transformed with plant transformation vector that does not contain the repABC element such as oriRi element of the present invention.

Thus, certain embodiments of the present invention provide methods involving use of repABC element such as oriRi from *Agrobacterium rhizogenes* and repABC origin from plasmid p42b of *Rhizobium etli*, including the sequences set forth herein, to reduce the frequency of plants transformed with non-T-DNA vector region. The present invention is also directed to the use of repABC element such as oriRi from *Agrobacterium rhizogenes* and repABC origin from plasmid p42b of *Rhizobium etli*, including the sequences set forth herein, to increase the frequency of one- or two-copy T-DNA transformation events. In some embodiments, both methods are employed in combination to achieve transformation events having lower frequencies of backbone incorporation and higher frequencies of one- or two-copy T-DNA transformation events.

EXAMPLES

The following examples are provided to better elucidate the practice of the present invention and should not be interpreted in any way to limit the scope of the present invention. Those skilled in the art will recognize that various modifications, additions, substitutions, truncations, etc., can be made to the methods and genes described herein while not departing from the spirit and scope of the present invention.

Example 1

Preparation of Vectors

Cloning steps followed standard protocols described by Sambrook et al. (1989). The 5.6 kb oriRi fragment, excised from pCGN1589 with DraI digestion, was used to replace the oriV fragment of pMON67438 that was digested with PshAI and BstXI and blunted with T4 DNA polymerase. This resulted in an oriRi base vector pMON83856 (FIG. 1). The 5.6 kb oriRi testing vector pMON83882 (FIG. 2) was made by insertion of the gus and CP4 fragments from the oriV control vector pMON67438, sequentially digested with AccI (blunted)/BamHI, into pMON83856 that had been opened with PmeI/BamHI. To truncate the oriRi fragment, two primers, 5' CACGTGTACAAGGTAGAATCCGCCT-GAG 3' (oriRi 5' promoter upstream; SEQ ID NO:5) and 5' GTATACAGGCTCTCCTTCACGATCAAC 3' (oriRi 3' after repC: SEQ ID NO:6), were synthesized and PCR was performed with high fidelity pfu polymerase and pMON83856 as a template. The PCR product was purified and inserted into pMON83930, which was digested with AfeI and XhoI and blunted with T4 DNA polymerase, to replace oriV fragment. The resulting vector pMON83934 (FIG. 3), with the truncated oriRi, was then confirmed by DNA sequencing. In order to make the testing vector pMON83937 (FIG. 4) with a truncated oriRi, pMON83934 was opened with KpnI, blunted with T4 DNA polymerase, and followed by BamHI digestion; the gus and Cp4 fragment from oriV control vector pMON67438 was sequentially digested with AccI, filled in with T4 DNA polymerase, and then further digested with BamHI. The two fragments were ligated with T4 DNA ligase and resulted in pMON83937.

Figure 5:
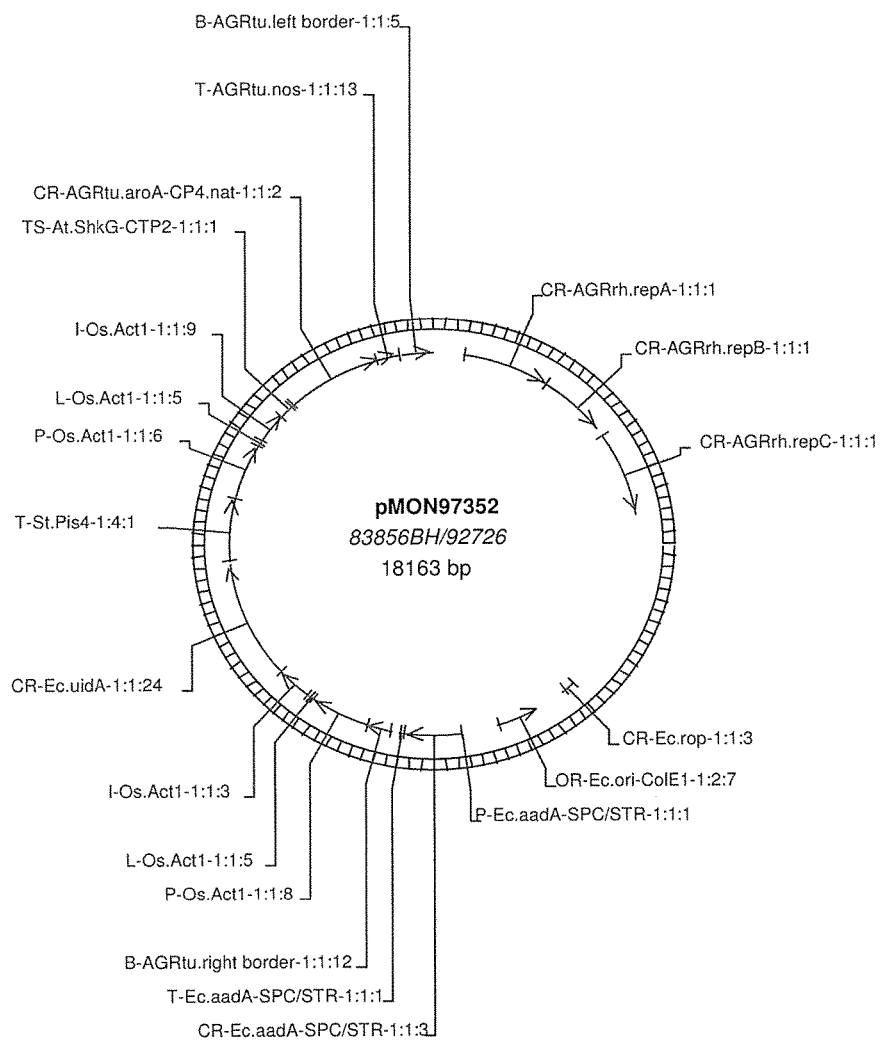
FIG. 5 shows a plasmid map of pMON97352, a test vector with a 5.6 kb oriRi fragment and CP4 selectable marker gene and GOI (gus), as an example, for corn transformation.
Figure 6:
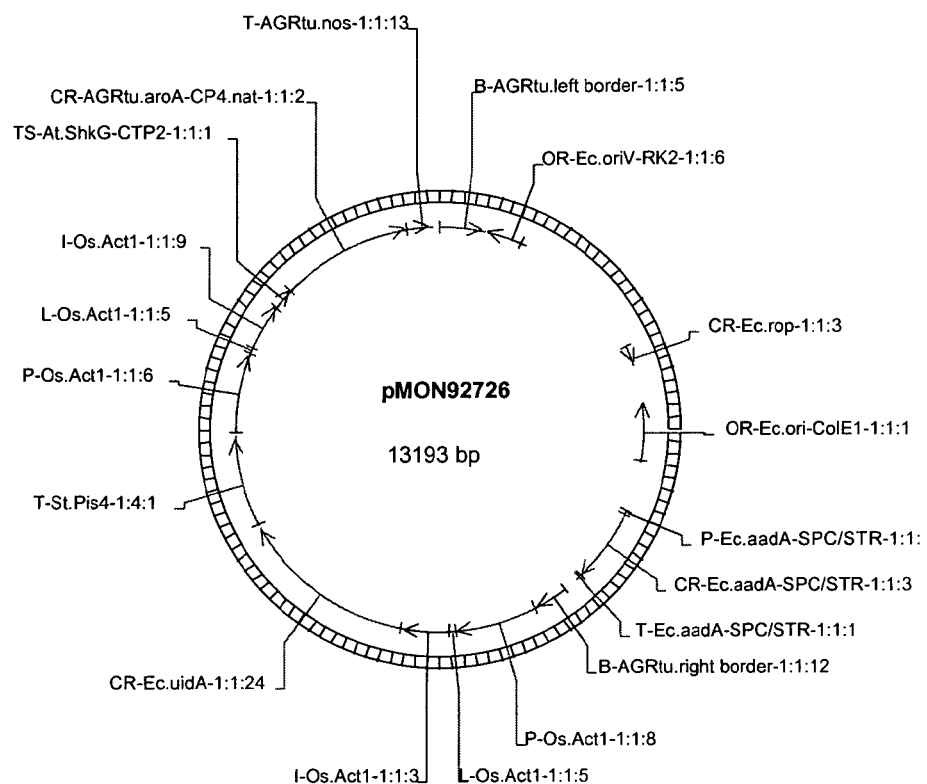
FIG. 6 shows a plasmid map of pMON92726 which was used as a control for corn transformation. It contains the same gene structure as pMON97352 except for the replication origin. It contains oriV instead of oriRi.

To construct the corn transformation vector pMON97352 (FIG. 5), a linker sequence containing SpeI and PspOMI sites were synthesized by annealing two oligos 5'-AGCT-TGGGCCCCTCGAGGCTAGCACTAGTG-3' (SEQ ID NO:7 and 5'-GATCCACTAGTGCTAGCCTCGAGGGGC-CCA-3' (SEQ ID NO: 8), and inserted into pMON83856 with the BamHI and HindIII digestion. The resulting intermediate oriRi vector was opened with SpeI and PspOMI and ligated with the CP4 and gus expression cassettes excised from pMON92726 (FIG. 6) with NotI and SpeI digestion (see FIG. 5, pMON97352). The oriV parental vector pMON992726 was used as a control vector to compare with corn oriRi test vector pMON97352.

Figure 7:
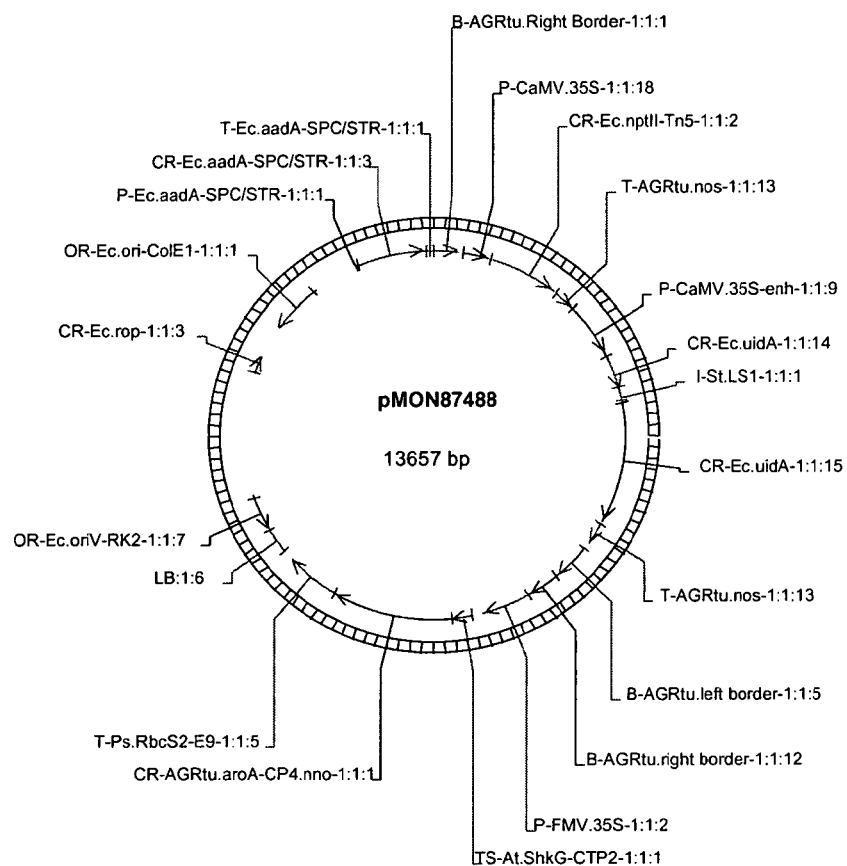
FIG. 7 shows a plasmid map of pMON87488, a 2 T-DNA transformation vector, which was used as a control for soybean transformation. It contains oriV instead of oriRi.
Figure 8:
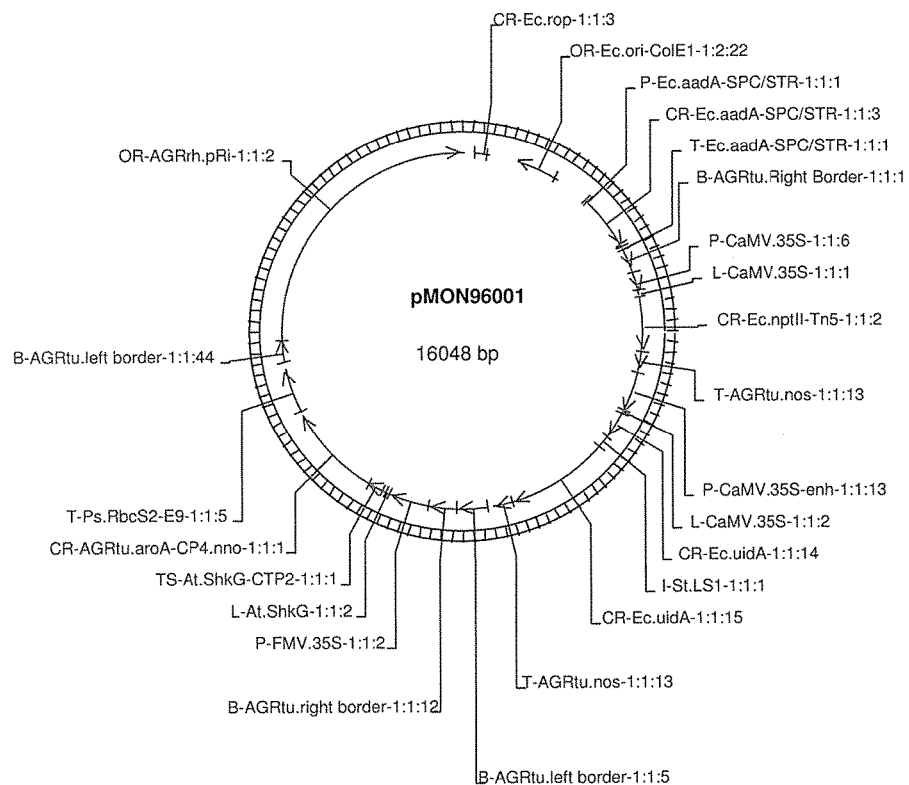
FIG. 8 shows a plasmid map of pMON96001, a 2 T-DNA transformation test vector with a 4.3 kb oriRi fragment and CP4 selectable marker gene and GOI (gus), as an example, for soybean transformation.
Figure 9:
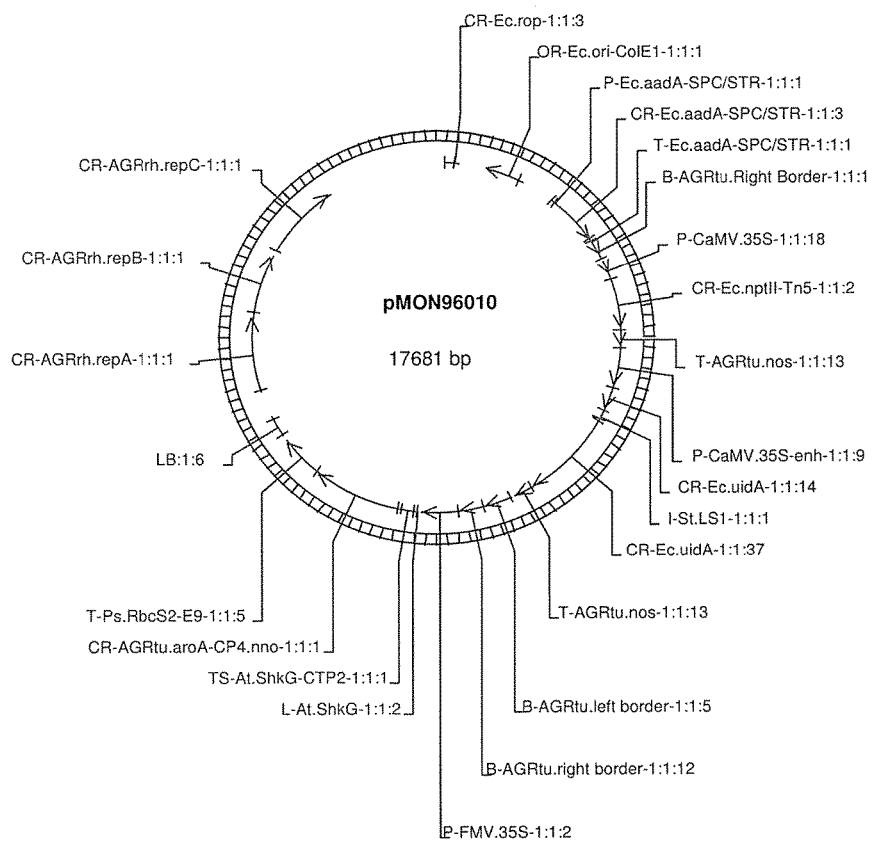
FIG. 9 shows a plasmid map of pMON96010, a 2 T-DNA transformation test vector with a 5.6 kb oriRi fragment and CP4 selectable marker gene and GOI (gus), as an example, for soybean transformation.

To construct oriV 2T control vector pMON87488 (FIG. 7), the octopine right border was excised from pMON51676, blunted with T4 DNA polymerase and inserted into pMON87485 which was opened with SalI/SpeI, filled-in with T4 DNA polymerase and CIP treated. To make the oriRi 2T vectors, pMON96001 (FIG. 8) and pMON96010 (FIG. 9), the oriV in pMON87488 was removed with AfeI and XhoI, the vector was filled-in with T4 DNA polymerase and inserted with the 4.2 kb oriRi replicon from pMON83934 obtained by digesting pMON83934 with PmlI and BstZ17I, resulting into pMON96001. The 5.6 kb oriRi replicon from pCGN1589 obtained by digesting it with DraI digestion was inserted to yield pMON96010.

Example 2

Soybean Crop Transformation

Transformation of soybean cells and regeneration of the cells into intact fertile plants by *Agrobacterium*-mediated transformation can be conducted using various methods known in the art. A method for soybean transformation (e.g. U.S. Pat. Nos. 6,384,301 and 7,002,058) was utilized with an organogenesis process.

Figure 2:
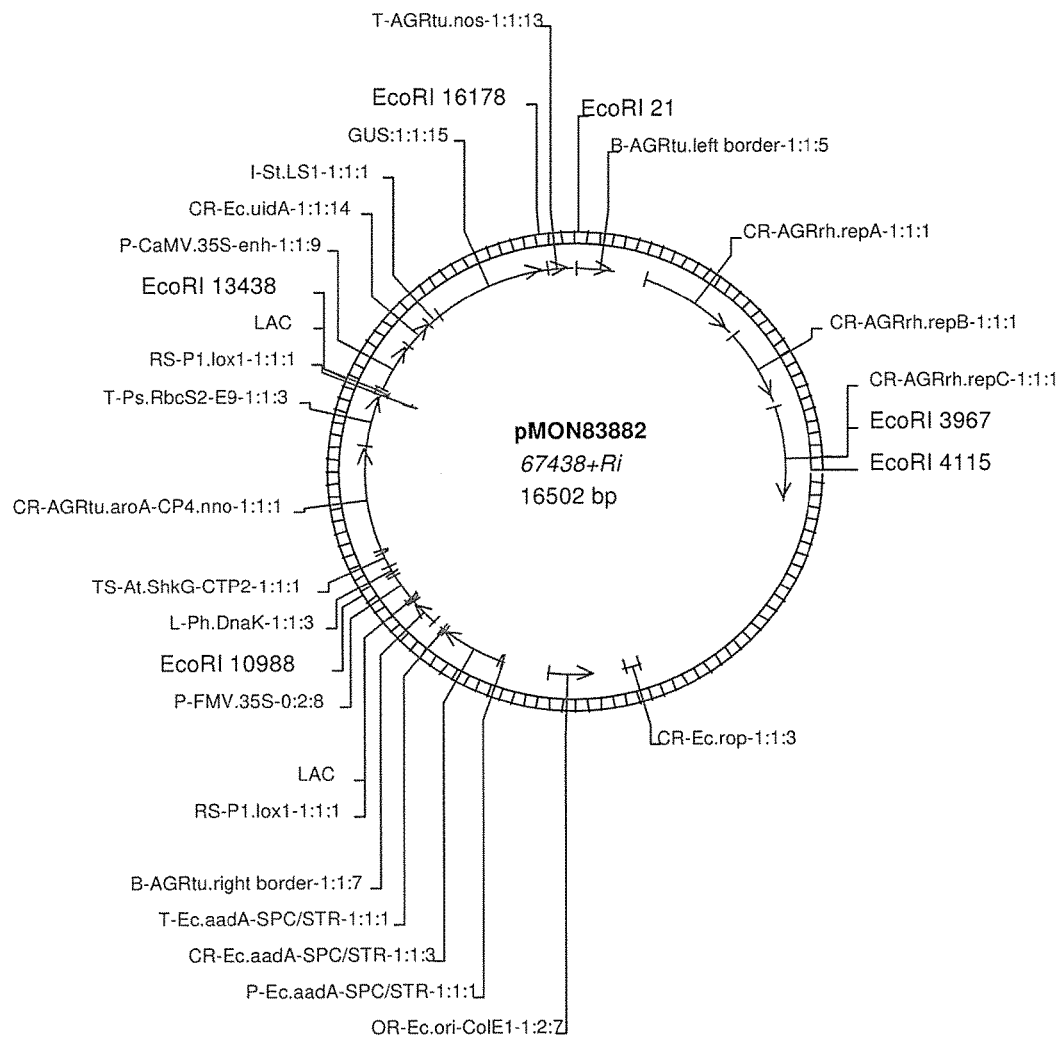
FIG. 2 shows a plasmid map of pMON83882, the testing vector with a 5.6 kb oriRi fragment and 5-enolpyruvylshikimate-3-phosphate synthase (CP4-EPSPS) selectable marker gene and the uidA (gus) gene of interest, as an example, for soy transformation.
Figure 3:
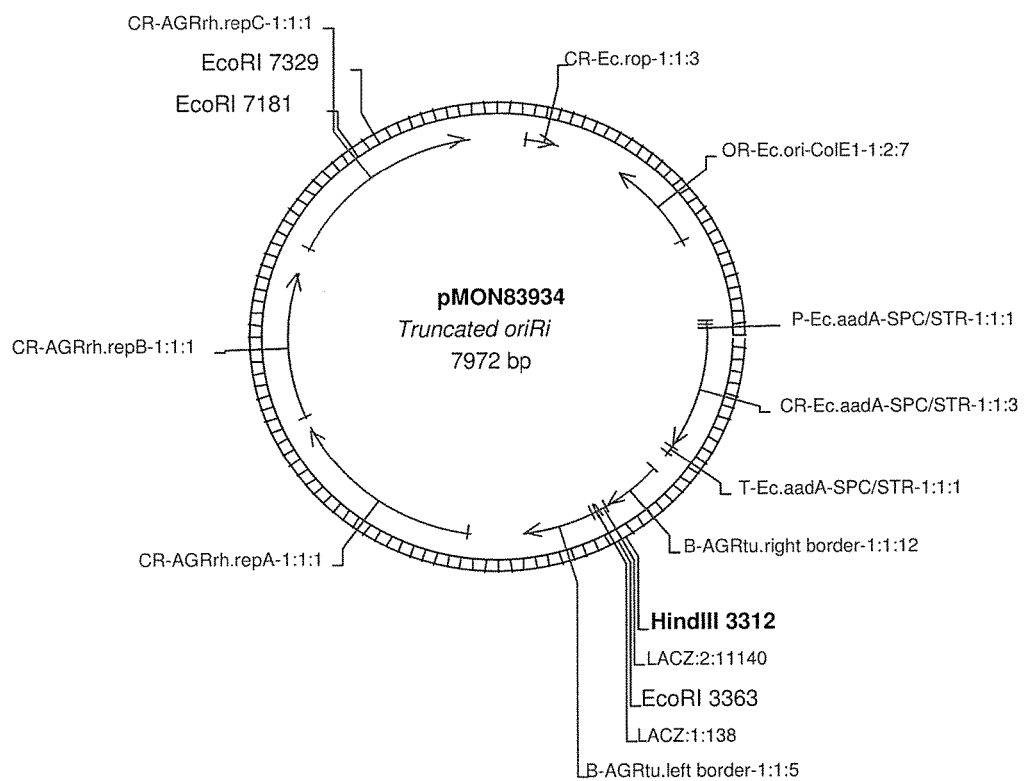
FIG. 3 shows a plasmid map of pMON83934, a base vector with a 4.2 kb oriRi fragment used for construction of pMON83937.
Figure 4:
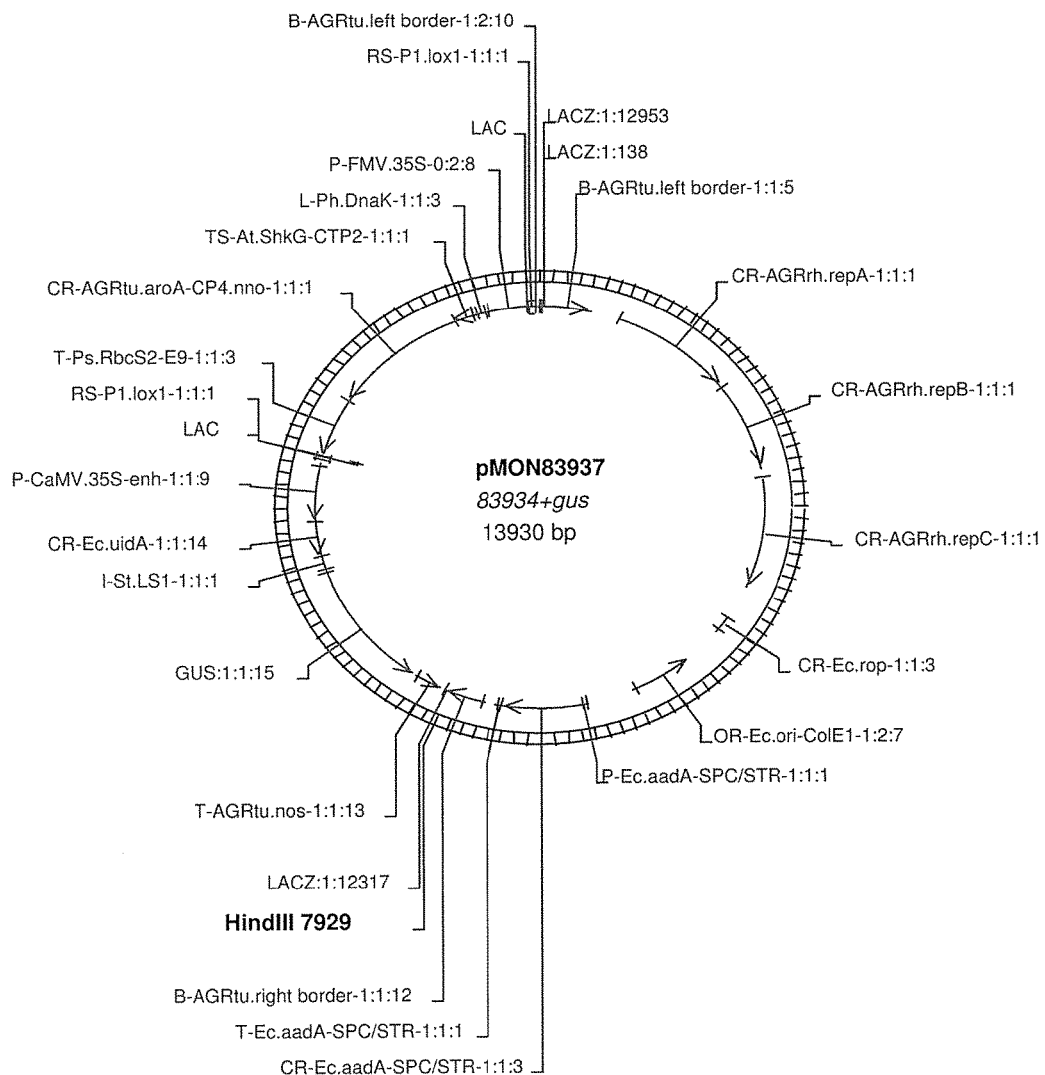
FIG. 4 shows a plasmid map of pMON83937, a testing vector with a 4.2 kb oriRi fragment and CP4 selectable marker gene and GOI (gus), as an example, for soy transformation.

The DNA constructs described in the present invention (e.g., plasmid pMON83882, substantially as shown in FIG. 2, and plasmid pMON83937, substantially as shown in FIG. 4) are transformed into a disarmed *Agrobacterium* strain ABI. The two oriV control vectors, pMON67438 and pMON83898 (same GOI but in different orientations), were also transferred into *Agrobacterium* cells. Two T DNA constructs and respective controls as described above were also used for transforming soybean. The DNA construct was transferred into *Agrobacterium* by electroporation. Single colonies were recovered on LB medium with spectinomycin 50 mg/l (for oriRi vectors) or 75 mg/l (for oriV vectors) and kanamycin 50 mg/l and inoculated in 20-50 ml liquid LB medium with same selection in a shaker with 200 rpm. The plasmid in the *Agrobacterium* was verified by restriction enzyme digestion of mini-prepared plasmid from 10 ml culture. The remainder of the liquid culture was mixed with glycerol to a final concentration of 20%, aliquoted and stored at −80 C as seed cultures.

To prepare the *Agrobacterium* inoculum for transformation, 0.25-1 ml frozen seed culture was inoculated into 250 or 500 ml LB medium with same antibiotic selection as above-mentioned and grown overnight at 26° C.-28° C. with shaking at 200 rpm to mid-log growth phase. The culture was spun down and directly suspended in an inoculation medium (INO medium) at the concentration of $OD_{660}$ about 0.3, as measured on a spectrophotometer.

Soybean cultivar A3525 was used for *Agrobacterium*-mediated transformation as described (e.g. U.S. Pat. No. 7,002,058). Soybean seeds were germinated for less than 14 hours at room temperature in BGM medium and the meristem explants from soy mature seeds were excised by machine as described in the US Patent Application 20050005321. For batch sonication, about 100 explants in PLANTCON lid were mixed with 20 ml of the *Agrobacterium* suspension in INO medium and sonicated in W-113 Sonicator for 20 seconds. For bulk sonication, about 1000 explants in plantcon lid were mixed with 100 ml of the *Agrobacterium* suspension in INO medium and sonicated for 20 seconds. After sonication, the explants were co-cultured in the same PLANTCON for 2-4 days at 23° C. with 16/8 hour light/dark period. Then the explants were transferred onto the surface of the WPM selection medium with 75 µM glyphosate. Each PLANTCON contained about 50 explants. After 2 weeks, explants were transferred again to 75 uM glyphosate solid WPM medium with primary radicle inserted in medium, each PLANTCON containing about 25 explants. Shoots with fully expanded trifolia recovered after 6-10 weeks post-inoculation were rooted in BRM medium with IAA 0.1 mg/l and 25 µM glyphosate selection. The rooted plantlets were transferred to greenhouse for maturity. Various media used for soybean transformation is detailed below in Table 1.

The above transformation and regeneration methods provides for plants that are greatly reduced in the occurrence of vector backbone DNA. Additionally, the plants have an added benefit of having reduced copy number of the insert T-DNA. The plants produced by the method are an aspect of the invention.

TABLE 1

Media components for soybean transformation

| BGM medium for soybean seed germination | |
|---|---|
| amount/L | Compound |
| 0.505 g | Potassium nitrate |
| 0.24 g | Ammonium nitrate |
| 0.493 g | Magnesium sulfate |
| 0.176 g | Calcium chloride |
| 27.2 mg | Potassium phosphate monobasic |
| 1.86 mg | Boric acid |
| 5.07 mg | Manganese sulfate |
| 2.58 mg | Zinc sulphate |

TABLE 1-continued

Media components for soybean transformation

| amount | Compound |
|---|---|
| 0.249 mg | Potassium iodide |
| 0.216 mg | Sodium Molybdate |
| 0.00025 mg | Copper sulphate |
| 0.00025 mg | Cobalt chloride stock |
| 3.36 mg | Disodium EDTA |
| 2.49 mg | Ferrous sulphate |
| 1.34 mg | Thiamine HCl |
| 0.5 mg | Nicotinic acid |
| 0.82 mg | Pyridoxine HCl |
| 20 g/L | Sucrose (Ultra Pure) |
| 1.29 g | Calcium Gluconate (Sigma #G4625) |
| 60 mg | Benomyl |
| pH | 5.6 |

INO medium for soy co-culture

| amount/L | Compound |
|---|---|

1/10 B5 medium components

| 1 g | Potassium Nitrate ($KNO_3$) |
|---|---|
| 30 g | Glucose |
| 3.9 g | MES (pH 5.4) |

After autoclaving, lipoic acid added to inoculum to final concentration 250 µM

SOY WPM shooting medium

| amount/L | Compound |
|---|---|
| 2.41 g | WPM Powder (Phytotech Lab) |

Add the WPM into water with stirring on a magnetic stirrer.
After dissolving, add following compounds sequentially:

| 20 g | Sucrose (Ultra Pure) |
|---|---|
| 1.29 g | Calcium Gluconate (Sigma) |
| 60 mg | Benomyl (or no fungicide) |
| 4.0 g | AgarGel (pH 5.6) |

| mL/L | Post-autoclaving ingredients |
|---|---|
| 4 mL | Cefotaxime (50 mg/mL) |
| 1 ml | Ticarcillin (100 mg/ml) |
| 5 mL | Carbenicillin (40 mg/mL) |
| 0.15 mL | Glyphosate (0.5 FS Stock) (0.075 mM) |

BRM rooting medium

| amount/L | Compound |
|---|---|
| 2.15 g | MS Powder (Gibco/Invitrogen) |
| 0.1 g | myo—Inositol |
| 2 mg | Glycine |
| 0.5 mg | Nicotinic acid |
| 0.5 mg | Pyrodoxine HCl |
| 0.5 mg | Thiamine HCl |
| 30 g | Sucrose (Ultra Pure) |
| 10 ml | L-Cysteine (10 mg/ml) |
| 8 g | Washed Agar |

| mL/L | Post-autoclaving ingredients |
|---|---|
| 5.0 | IAA (0.033 mg/ml in 1 mM KOH) |
| 1 mL | Ticarcillin (100 mg/ml) |

TABLE 1-continued

Media components for soybean transformation

| 0.05 mL | Glyphosate (0.5 FS Stock) (0.025 mM) |
|---|---|
| 0.1 mL | IAA (1.0 mg/ml) |

Other dicot plant cells can be transformed and regenerated into intact plants by methods known in the art of plant transformation and tissue culture. The use of *Agrobacterium*-mediated methods to transfer the T-DNA of the plasmids of the present invention are well known in the art. For example cotton (U.S. Pat. Nos. 5,004,863; 5,159,135; 5,518, 908, 5,846,797, and 6,624,344, herein incorporated by reference) and *Brassica* (U.S. Pat. No. 5,750,871).

Example 3

Corn Crop Transformation

Two vectors, pMON97352 (oriRi, single copy in *Agrobacterium*) and pMON92726 (oriV, multiple copies in *Agrobacterium* as a control) containing same plant selectable marker gene CP4 and gus gene cassettes, both driven by rice actin promoters (FIG. 5), were electroporated into *Agrobacterium tumefaciens* strain ABI for corn transformation. *Agrobacterium* containing the vector in glycerol stock was streaked out on solid LB medium supplemented with antibiotics (all in active ingredient) kanamycin (40 mg/L), spectinomycin (31 mg/L), streptomycin (38 mg/L) and chloramphenicol (25 mg/L) and incubated at 28° C. for 2 days. Two days before *Agrobacterium* inoculation of the maize immature embryos, one colony or a small loop of *Agrobacterium* from the *Agrobacterium* plate was picked up and inoculated into 25 mL of liquid LB medium supplemented with 62 mg/L of spectinomycin and 40 mg/L of kanamycin in a 250 mL flask. The flask was placed on a shaker at approximately 150-200 rpm and 27-28° C. overnight. The *Agrobacterium* culture was then diluted (1 to 5) in the same liquid medium and put back on the shaker. Several hours later, one day before inoculation, the *Agrobacterium* cells were spun down at 3500 rpm for 15 min. The bacterium cell pellet was re-suspended in induction broth with 200 µM of acetosyringone and 50 mg/L spectinomycin and 25 mg/L kanamycin and the cell density was adjusted to 0.2 at $OD_{660}$. The bacterium cell culture (50 mL in each 250 mL flask) was then put back on the shaker and grown overnight. On the morning of inoculation day, the bacterium cells were spun down and washed with liquid 1/2 MS VI medium (Table 2) supplemented with 200 µM of acetosyringone. After one more centrifugation, the bacterium cell pellet is re-suspended in 1/2 MS PL medium (Table 2) with 200 µM of acetosyringone (Table 2) and the cell density was adjusted to 1.0 at $OD_{660}$ for inoculation.

Reagents are commercially available and can be purchased from a number of suppliers (see, for example Sigma Chemical Co., St. Louis, Mo.).

TABLE 2

Media used in Example 3

| Component | 1/2 MSVI | 1/2 MSPL | Co-culture medium | Induction MS | MSW50 | MS/6BA | MSOD |
|---|---|---|---|---|---|---|---|
| MS salts | 68.5 g/L | 68.5 g/L | 2.2 g/L | 4.4 g/L | 4.4 g/L | 4.4 g/L | 4.4 g/L |
| Sucrose | 20 g/L | 68.6 g/L | 20 g/L | 30 g/L | 30 g/L | 30 g/L | — |
| Maltose | — | — | — | — | — | — | 20 g/L |
| Glucose | 10 g/L | 36 g/L | 10 g/L | — | — | — | 10 g/L |

TABLE 2-continued

Media used in Example 3

| Component | ½ MSVI | ½ MSPL | Co-culture medium | Induction MS | MSW50 | MS/6BA | MSOD |
|---|---|---|---|---|---|---|---|
| l-Proline | 115 mg/L | 115 g/L | 115 g/L | 1.36 g/L | 1.38 g/L | 1.36 g/L | — |
| Casamino Acids | — | — | — | 50 mg/L | 500 mg/L | 50 mg/L | — |
| Glycine | 2 mg/L | 2 mg/L | 2 mg/L | — | 2 mg/L | — | — |
| l-Asparagine | — | — | — | — | — | — | 150 mg/L |
| myo-Inositol | 100 mg/L | 100 mg/L | 100 mg/L | — | 100 mg/L | 100 mg/L | 100 mg/L |
| Nicotinic Acid | 0.5 mg/L | 0.5 mg/L | 0.5 mg/L | 1.3 mg/L | 0.5 mg/L | 1.3 mg/L | 1.3 mg/L |
| Pyridoxine HCl | 0.5 mg/L | 0.5 mg/L | 0.5 mg/L | 0.25 mg/L | 0.5 mg/L | 0.25 mg/L | 0.25 mg/L |
| Thiamine HCl | 0.1 mg/L | 0.1 mg/L | 0.6 mg/L | 0.25 mg/L | 0.6 mg/L | 0.25 mg/L | 0.25 mg/L |
| Ca Pantothenate | — | — | — | 0.25 mg/L | — | 0.25 mg/L | 0.25 mg/L |
| 2,4-D | — | — | 3 mg/L | 0.5 mg/L | 0.5 mg/L | — | — |
| Picloram | — | — | — | 2.2 mg/L | — | — | — |
| Silver Nitrate | — | — | 1.7 mg/L | 1.7 mg/L | — | — | — |
| BAP | — | — | — | — | — | 3.5 mg/L | — |

Media ½ MSVI and ½ MSP were used as liquid. Co-culture medium was solidified with 5.5 mg/L low EEO agarose. All other media were solidified with 3 g/L phytagel for glyphosate selection.

Corn line LH244 (U.S. Pat. No. 6,252,148) was used in this study. Ears containing immature embryos were harvested and kept refrigerated at 4° C. until use. Immature embryos were isolated from surface sterilized ears and directly dropped into the prepared *Agrobacterium* cell suspension in microcentrifuge tube and inoculated for 5 to 20 min. After *Agrobacterium* cell suspension was removed using a fine tipped sterile transfer pipette, the immature embryos were transferred onto the co-culture medium (Table 2). The embryos were cultured in a dark incubator (23° C.) for approximately 24 h.

After the co-cultivation, the embryos were transferred onto a modified MS medium (Induction MS, Table 2) supplemented with 500 mg/L carbenicillin and 0.1 mM glyphosate at 30° C. for 2 weeks followed by an additional week in a dark culture room at 27-28° C. All the callus pieces were then transferred individually onto the first regeneration medium, the same medium mentioned above except 2,4-D and picloram were replaced by 3.5 mg/L BAP (MS/6BA, Table 2) and the carbenicillin level was dropped to 250 mg/L. The cultures were moved to a culture room with 16-h light/8-h dark photoperiod and 27° C. After 5-7 days, the callus pieces were transferred onto the second regeneration medium (MSOD, Table 2). In another 2 weeks, the callus pieces that had shoots regenerated were transferred onto the same hormone-free medium in Phytatrays™ for further growth. Regenerated plants (RO) with one or more healthy roots were moved to soil in peat pots in a growth chamber. In 7 to 10 days, they were transplanted into 12-inch pots and moved to a greenhouse with conditions for normal corn plant growth. The plants were either self-pollinated or crossed with wild-type plants.

Example 4

Molecular Analysis for Backbone DNA and Copy Number

A. Soybean Transformed with One T-DNA Constructs

DNA was extracted from tissue samples collected from greenhouse grown plants transformed with the DNA plasmids of the present invention. A PCR-based method was used to assay the DNA for the presence of the oriRi sequence using repA forward primer 5'-ACAAGGTAGAATCCGC-CTGAG-3' (Xd487b; SEQ ID NO:11) and repA reverse primer 5'-TTCAACTCTGGCATCTCAGAC-3' (Xd488; SEQ ID NO:12) as an indicator of vector backbone. This DNA is adjacent to the LB and its presence in the DNA extracted from the regenerated plants indicates that transfer of vector sequences beyond the LB has occurred. DNA can be isolated from plant tissues by any number of methods for example, the CTAB procedure (Rogers et al., 1985) or DNAeasy™ 96 Plant Kit (Cat. #69181, Qiagen Inc., Valencia, Calif.) following the manufacturers instructions. Taqman® (PE Applied Biosystems, Foster City, Calif.) is described as a method of detecting and quantifying the presence of a DNA sequence and is fully understood in the instructions provided by the manufacturer. DNA primer molecules (SEQ ID NO:11 and 12) were used in the described method to identify the oriRi DNA from plant extracts. The conditions and apparatus used can be modified by those skilled in the art to provide the same results.

Soybean meristem axis excised from mature seeds were transformed with a control DNA plasmid (pMON67438 or pMON83898) and a plasmid of the present invention (pMON83882 or pMON83937), then regenerated into intact plants. The intact plants were analyzed for the presence of the gene of interest (CP4) and non T-DNA oriRi and oriV sequences. Table 3 shows the results of this analysis.

Out of 39 plants tested, only 3 had vector backbone sequences, a frequency of 7.7%. In comparison, the control plasmid (an oriV plasmid) exhibited a vector backbone frequency of from 21% to 25% (depending on which samples were considered). This difference was quite dramatic and entirely unexpected.

Another important component of a commercially viable transgenic plant is the occurrence of low insert complexity. This is often referred to as "low copy number." It is difficult to select progeny and to successfully breed the transgenic trait if the copy number of the insert is too high. Ideally, only a single copy of the transgene would be present in a transgenic event.

Copy number can be determined by several methods known in the art of molecular biology. Southern blot analysis is the most commonly used method. Methods using the Invader® technology (Third Wave Inc. Madison, Wis.) are also used for determining copy number of T-DNA inserts in transgenic plants.

The soybean plant cells were transformed with a control DNA plasmid (pMON67438) and a plasmid of the present invention (pMON83882), then regenerated into intact plants, as described above. The resulting transgenic plants were analyzed for copy number using two different methods: 1) "Invader CP4" method and 2) Southern blotting. The results are shown in Table 3.

TABLE 3 pRi ori vector backbone effects on transformation frequency, copy number, and the insert in soybean transformation.

| pMON | TF[a] | Backbone | Invader CP4 1 Copy | Invader CP4 1 + 2 Copy | Southern GUS Copy # |
|---|---|---|---|---|---|
| 83882 (5.6 kb oriRi) | 1.26% | 7.7% (3/39) oriRi | 41% (16/39) | 79.5% (31/39) | 56.4% (22/39) 1 Copy 33.3% (13/39) 2 Copy |
| 67438 (oriV) | 1.4% | 21% (8/38)[b] 25% (56/226)[c] oriV | 37% (14/38) 25% (57/226) | 60% (23/38) 63% (142/226) | N/A N/A |

[a]Pooled data from three side by side experiments.
[b]Plant number from side by side comparison.
[c]Pooled plant number of pMON67438 plants produced.

Using the "Invader CP4" method, the inventive plasmid, pMON83882, resulted in single-copy transformation events 41% of the time, as compared to the control plasmid pMON67438 which resulted in a single-copy transformation event only 25% of the time using pooled samples of other experiments or only 37% of the time using side by side experiments. Considering one- and two-copy events together, pMON83882 resulted in said events 79.5% of the time, as compared to 60% from side by side experiments and 63% from pooled samples employing the control plasmid. Using the Southern blotting comparison, pMON83882 produced one-copy events 56.4% of the time and 33.3% of the time two-copy events, for a total of nearly 90% one- and two-copy events combined. Again, these results were both dramatic and unexpected.

B. Molecular Analysis of Transgene Copy Number in Soybean Two T-DNA Transformants In order to analyze the oriRi impact on 2T-DNA transformation, the 4.2 kb oriRi 2T vector pMON96001 was side by side compared with the oriV 2T vector pMON87488 for six times. The 5.6 kb oriRi 2T vector pMON96010 was also included in the last two comparison experiments in these preliminary experiments (Table 4, Group A). Total DNA was extracted from seed segments of mature seeds harvested from greenhouse and used to determine transgene copy number by Invader technology using CP4 probe and NOS probes. CP 4 Invader® detection assay used the following sequence as a targeting site: 5' TCGCTTTCCTTGACGCG-GAGTTCTTCCA GACCGTTCAT CACGG 3' (SEQ ID NO: 13) and GTAGGTGATTGGCGTTG (SEQ ID NO:14) as a probe sequence. NOS Invader® detection assay used the following nos 3' sequence as a targeting site TGAATTACGTTAAGCATGTAATAATTAACATGTAATGCATGACT (SEQ ID NO:15 and GTTATTTATGAGATGGGTTTTTATGA (SEQ ID NO:16) as NOS Invader® probe sequence.

The 1 and/or 2 copy transformants were increased from 35% in the control oriV vector to over 40% in both oriRi vectors. The frequency of marker-free plants in RO plants (marker free events/total RO plants) was increased from 4.76% in the oriV control vector to 16.4% and 18.4%, respectively, in the two oriRi vector. Overall, the marker-free transformation frequency (marker free events/initial explant number) more than doubled in the two oriRi 2T vectors compared to the oriV 2T vector.

Additional in-parallel experiments with larger initial explant number were further used to compare the oriV control 2T vector with the 4.2 kb oriRi 2T vector (Table 4, Group B). The oriRi 2T vector reproduced the results: the 1+2 copy event frequency and the marker free frequency (MF %) are both increased and the marker-free transformation frequency is more than doubled in the oriRi vector. The results indicated that the oriRi 2T vectors are significantly more efficient to produce marker free plants than the oriV 2T vector by increasing low copy events and improving marker free transformation frequency.

TABLE 4

Effect of type of origin of replication on 2T-DNA vector transformation of soybean.

| Construct | Explant Total | R0 plant # | TF[1] (%) | 1 + 2 copy[2] Co-T | MF Events[3] (analyzed) | MF %[4] plants | MF TF[5] |
|---|---|---|---|---|---|---|---|
| Group A | | | | | | | |
| pMON87488 (oriV) | 4318 | 84 | 1.95 | 32.9% (25/76) | 4 (25) | 4.76% (4/84) | 0.09% |
| pMON96001 (4.2 kb oriRi) | 4757 | 67 | 1.41 | 42.4% (25/59) | 11 (24) | 16.41% (11/67) | 0.23% |
| pMON96010 (5.6 kb oriRi) | 1575 | 38 | 2.41 | 41.7% (15/36) | 7 (15) | 18.42% (7/38) | 0.44% |
| Group B | | | | | | | |
| pMON87488 (oriV) | 11024 | 145 | 1.31 | 35.7% (30/84) | 9 (30) | 6.2% (9/145) | 0.08% |

TABLE 4-continued

Effect of type of origin of replication on 2T-DNA vector transformation of soybean.

| Construct | Explant Total | R0 plant # | TF[1] (%) | 1 + 2 copy [2] Co-T | MF Events [3] (analyzed) | MF % [4] plants | MF TF [5] |
|---|---|---|---|---|---|---|---|
| pMON96001 (4.2 kb oriRi) | 8660 | 107 | 1.24 | 43.8%% (39/89) | 16 (38) | 14.95% (16/107) | 0.18% |

Note:
[1] TF: transformation frequency = R0 plants/total explants;
[2] 1 + 2 copy Co-T: 1 and/or 2 copy gus and CP4 marker 2 T-DNA co-transformants. Only 1-2 copy events were further advanced to analyze the marker segregation in seeds;
[3] MF events: gus gene positive, marker-free events from the 1 + 2 copy co-transformants analyzed by seed segregation;
[4] MF % plants: gus positive, marker free plants/R0 plant #;
[5] Marker-free transformation frequency (MF TF) = unlinked event #/initial explant #.

Figure 10:
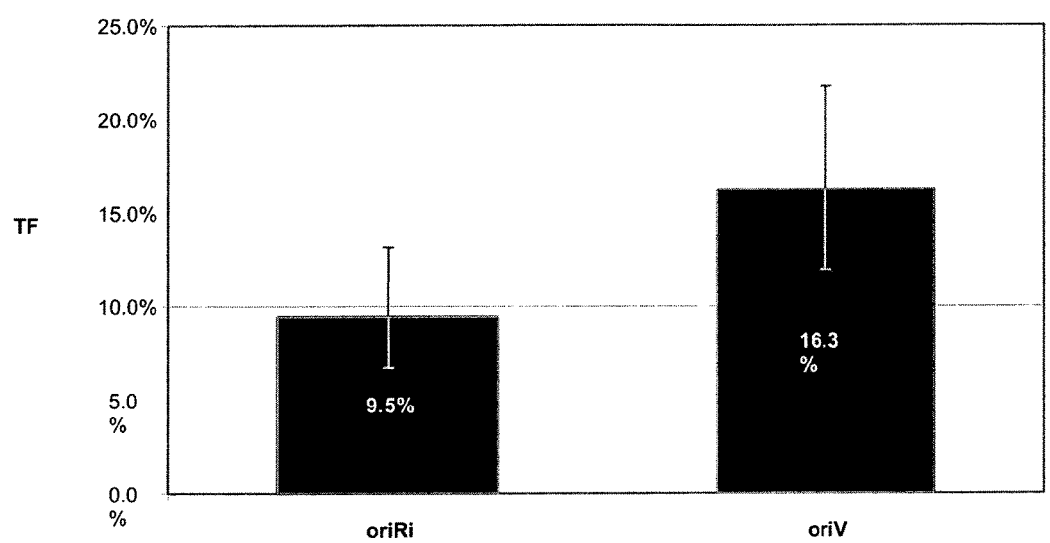
FIG. 10 shows the effect of type of replication origin on transformation frequency in corn. Error bars represent the 95% confidence interval; * indicates a significant difference between oriRi (pMON97352) and oriV (pMON92726).

C. Molecular Analysis of Vector Backbone DNA and Transgene Copy Number in Corn Transformed with One T-DNA Constructs To investigate the oriRi replication origin effect on corn transformation, the 5.6 kb oriRi vector pMON97352 containing gus and CP4 genes, both driven by rice actin promoter, was compared to the oriV vector pMON92726 with the same T-DNA structure containing gus and CP4 genes. Corn immature embryos from Cultivar LH244 were inoculated with *Agrobacterium* containing either the oriRi or the oriV vector in parallel. Each treatment consisted of about 110 embryos. In total 16 side by side comparison experiments were initiated. The oriRi vector showed significantly lower transformation frequency than the oriV control vector (FIG. 10) with average TF 9.5% and 16.3% for oriRi and oriV vectors, respectively. However, the overall transformation efficiency with oriRi and oriV vectors was same.

The presence of backbone sequence in transgenic corn plants was determined by Endpoint TaqMan® assay (Applied Biosystems, Foster City, Calif.). for the oriRi or oriV sequence, LB sequences that are 3' flanking for short read-through close to the LB nicking site and RB sequences that are 5' flanking before the RB nicking site for intact backbone readthrough. The oriV primers 5' AACGCCTGATTT-TACGCGAG 3' (forward; SEQ ID NO: 17) and 5' CAATACCGCAGGGCACTTATC 3' (reverse; SEQ ID NO:18), with probe CCCACAGATGATGTGGAC (SEQ ID NO:19) labeled with fluorescent dye 6-FAM at the 5' end. The oriRi primers are 5' TGGCAAGGAATGGGTTTGAG 3' (forward; SEQ ID NO:20) and 5' CTACAACTACAG-GCGCTGCTTTT 3' (reverse; SEQ ID NO:21) with the probe 6-FAM-TGGCGAAGTCTGTCC (SEQ ID NO:22) to detect oriRi sequence 621 bp downstream of LB nicking site. The RB 5' flanking primers are 5' GCCAAGGGATCTTTTTGGAAT 3' (forward; SEQ ID NO:23) and 5' CCACCCAAACGTCGGAAA 3' (reverse; SEQ ID NO:24) with the probe 6FAM-TGCTC-CGTCGTCAGG (SEQ ID NO:25) to detect 5' RB flanking 186 bp before the RB nicking site. The primers for detecting LB 35 bp downstream of the LB nicking site were 5' GCACCCGGTGGAGCTT 3' (forward; SEQ ID NO:26) and 5' TCTGCCTAACCGGCTCAGT 3' (reverse; SEQ ID NO:27) with the probe CATGTTGGTTTCTACGCAG (SEQ ID NO:28) labeled with fluorescent dye 6-FAM at the 5' end. Approximately 10 ng DNA was used for Endpoint TaqMan® reaction according to the manufacturer's instruction (Applied Biosystems, Foster City, Calif.).

Figure 11:
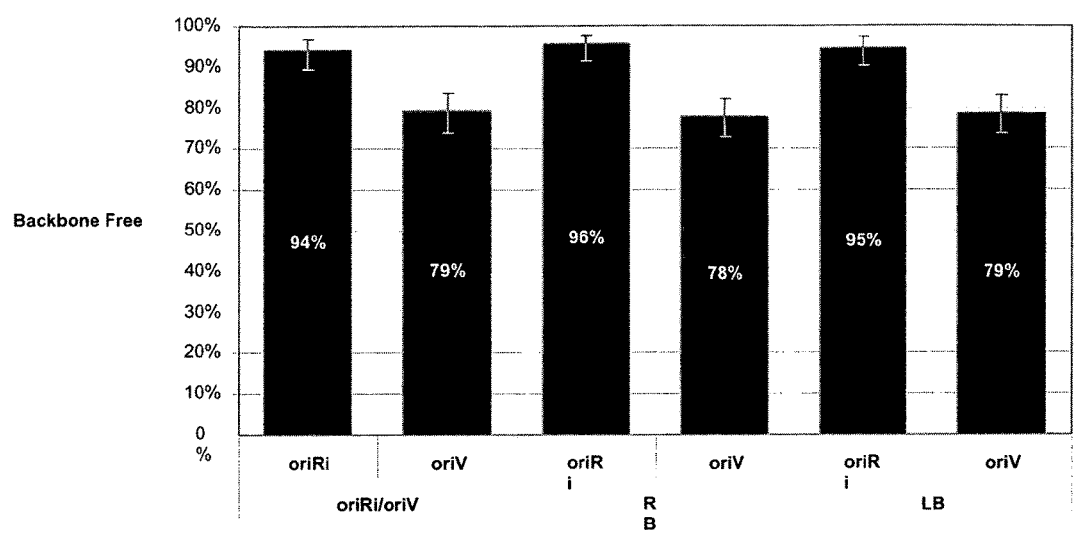
FIG. 11 shows the effect of type of replication origin on backbone sequence transfer in corn transformation. Error bars represent the 95% confidence interval; * indicates a significant difference between oriRi (pMON97352) and oriV (pMON92726). oriRi/oriV, RB, and LB indicates the type of backbone probe used.

As shown in FIG. 11, about 95% of the transgenic plants derived from oriRi vector were backbone-free, which is significantly better than oriV vector control showing about 78% backbone free frequency. Since the vector backbone starts at LB after nicking site and ends before RB nicking site, use of three different backbone probes (LB downstream, oriRi/oriV and RB upstream) in both oriRi and oriV vector derived plants revealed that most vector backbone transferred contained entire vector backbone sequence.

The CP4 transgene copy number was determined by Invader® assay according to the manufacturer's instruction (Third Wave Technologies Inc. Madison, Wis.) using the a CP4 sequence. The gus transgene copy number was measured by determining the gus cassette transcriptional terminator pinII (shown as Pis 4 in FIGS. 5 and 6) using TaqMan® technology (Applied Biosystems, Foster City, Calif.). The pinII TaqMan® primers were 5' ATGAAATAAAAGGATGCACACAT 3' (forward; SEQ ID NO:29) and 5' ACAACTTTGATGCCCACATT 3' (reverse; SEQ ID NO:30) with the probe TGACATGCTAATCAC- (SEQ ID NO:31) labeled with fluorescent dyes 6-FAM at the 5' end and MGBNFQ at the 3' end.

Figure 12:
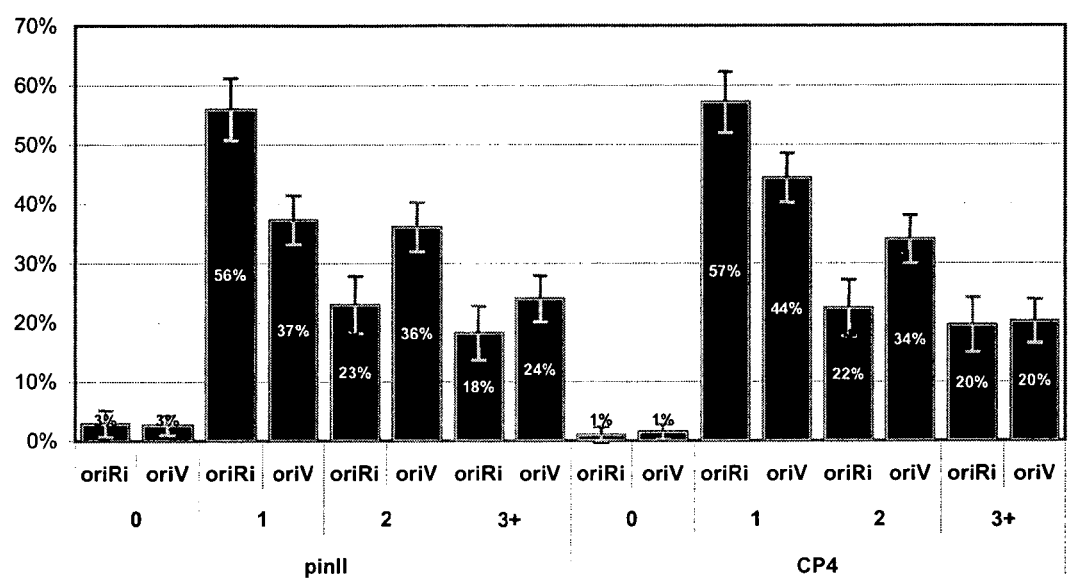
FIG. 12 shows the effect of type of replication origin on transgene quality in corn transformation. Error bars represent the 95% confidence interval. 0, 1, 2, 3+ indicates copy number.

FIG. 12 shows the transgene copy number assay results. The oriRi vector significantly increased single copy plant frequency compared to the control oriV vector, while the frequency of 2 or more copy events in oriRi vector was decreased. Both TaqMan® and Invader® assays with two different probes showed similar results. Since the single copy backbone free plants are the most valuable for both research and development, the oriRi vector increasing the single copy frequency and decreasing backing containing events in corn represents a significant improvement for quality in transgenic event production.

Example 5

Construction of Plant Transformation Vector Containing repABC Replication Origin from *Rhizobium*

Figure 13:
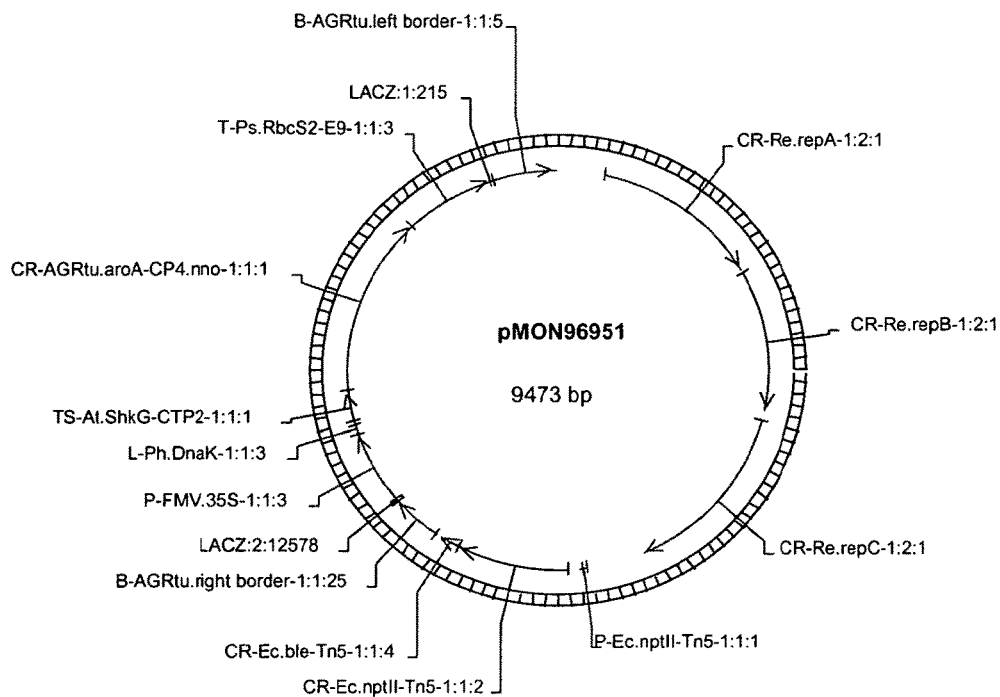
FIG. 13 shows a plasmid map of pMON96951 containing repABC replication origin from *Rhizobium etli* CFN42 p42b plasmid and CP4 EPSPS selectable marker gene for soybean.

To clone repABC replication origin from *Rhizobium etli* CFN42 strain, the USDA strain was obtained from USDA *Rhizobium* Collection Center. A 4.3 kb repABC fragment was amplified from *R. etli* plasmid p42b found in strain CFN42 by PCR with primers 5' C<u>CACGTG</u>AGTTACGGCTGATCGACCAGAC 3' (Xd745; SEQ ID NO:9) and 5' G<u>CCTAGG</u>ACGTCAACTCCAACCGCACCGT 3' (Xd746; SEQ ID NO:10) and ligated to TOPO blunt cloning vector (Invitrogen, Carlsbad, Calif., USA), which resulted in pMON96941 and was confirmed by sequencing. The repABC fragment was digested with PmlI and AvrII (shown by underlined sequence in primers) and ligated to pMON96948 opened with SmaI and AvrII. The ligate was directly transferred into *Agrobacterium tumefaciens* AB2 (a kanamycin sensitive strain) competent cells, and plated onto LB plate with kanamycin 50 mg/l. The kan resistant colonies were inoculated into liquid LB medium with 50 mg/l kanamycin, and a plasmid DNA was prepared by miniprep. The construct was confirmed by restriction digestion. Since the vector pMON96951 does not contains an *E. coli* replication origin, it can not be maintained in *E. coli*.

pMON96951 (FIG. 13) is used for transforming plant species as described above. The transgenic events are analyzed for reduced vector backbone integration and high frequency of low-copy transformation events by methods described in Example 4.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

The following are herein incorporated by reference:
U.S. Pat. No. 4,581,847; U.S. Pat. No. 4,761,373; U.S. Pat. No. 4,810,648; U.S. Pat. No. 5,004,863; U.S. Pat. No. 5,013,659; U.S. Pat. No. 5,034,322; U.S. Pat. No. 5,094,945; U.S. Pat. No. 5,141,870; U.S. Pat. No. 5,159,135; U.S. Pat. No. 5,229,114; U.S. Pat. No. 5,273,894; U.S. Pat. No. 5,276,268; U.S. Pat. No. 5,304,730; U.S. Pat. No. 5,378,824; U.S. Pat. No. 5,463,175; U.S. Pat. No. 5,463,175; U.S. Pat. No. 5,512,466; U.S. Pat. No. 5,516,671; U.S. Pat. No. 5,518,908; U.S. Pat. No. 5,543,576; U.S. Pat. No. 5,561,236; U.S. Pat. No. 5,591,616; U.S. Pat. No. 5,597,717; U.S. Pat. No. 5,605,011; U.S. Pat. No. 5,608,149; U.S. Pat. No. 5,627,061; U.S. Pat. No. 5,633,435; U.S. Pat. No. 5,633,437; U.S. Pat. No. 5,633,444; U.S. Pat. No. 5,637,489; U.S. Pat. No. 5,646,024; U.S. Pat. No. 5,689,041; U.S. Pat. No. 5,716,837; U.S. Pat. No. 5,719,046; U.S. Pat. No. 5,750,871; U.S. Pat. No. 5,750,876; U.S. Pat. No. 5,767,366; U.S. Pat. No. 5,773,696; U.S. Pat. No. 5,824,877; U.S. Pat. No. 5,846,797; U.S. Pat. No. 5,939,602; U.S. Pat. No. 5,942,664; U.S. Pat. No. 5,958,745; U.S. Pat. No. 5,985,605; U.S. Pat. No. 5,998,700; U.S. Pat. No. 6,011,199; U.S. Pat. No. 6,013,864; U.S. Pat. No. 6,040,497; U.S. Pat. No. 6,063,597; U.S. Pat. No. 6,063,756; U.S. Pat. No. 6,072,103; U.S. Pat. No. 6,080,560; U.S. Pat. No. 6,093,695; U.S. Pat. No. 6,110,464; U.S. Pat. No. 6,121,436; U.S. Pat. No. 6,166,292; U.S. Pat. No. 6,171,640; U.S. Pat. No. 6,225,105; U.S. Pat. No. 6,228,992; U.S. Pat. No. 6,252,148; U.S. Pat. No. 6,268,549; U.S. Pat. No. 6,316,407; U.S. Pat. No. 6,380,466; U.S. Pat. No. 6,384,301; U.S. Pat. No. 6,414,222; U.S. Pat. No. 6,444,876; U.S. Pat. No. 6,476,295; U.S. Pat. No. 6,506,962; U.S. Pat. No. 6,531,648; U.S. Pat. No. 6,537,750; U.S. Pat. No. 6,613,963; U.S. Pat. No. 6,624,344; U.S. Pat. No. 7,002,058; U.S. Patent Pub. 2003/0028917; U.S. Patent Pub. 20040177399; U.S. Patent Pub. U.S. Patent Pub. 20030083480; U.S. Patent Pub. 20030115626; U.S. Patent Pub. 20050005321; U.S. Patent Pub. 20030135879; U.S. Prov. Appln. 60/800,872; PCT Appln. WO04074443; PCT Appln. WO04009761; PCT Appln. WO9927116; PCT Appln. WO8704181A1; PCT Appln. WO8900193A; PCT Appln. WO8911789; PCT Appln. WO 9638567; PCT Appln. WO05107437; PCT Appln. WO05003362

European Appln. 275,957
Japanese Appln. 06343473
Ammirato et al., In: *Handbook of Plant Cell Culture—Crop Species*, Macmillan Publ. Co., 1984.
Ausubel et al., In: *Current Protocols in Molecular Biology*, John, Wiley & Sons, Inc, NY, 6.3.1-6.3.6, 1989.
Binns and Howitz, In: *Bacterial Pathogenesis of plants and Animals*, Dang (Ed.), Berlin: Stringer Verlag, 119-138, 1994.
Broothaerts et al., *Nature*, 433:629-633, 2005.
Datta et al., *Bio/Technology*, 8:736-740, 1990.
Fraley et al., *Bio/Technology*, 3:629-635, 1985.
Fromm, UCLA Symposium on Molecular Strategies for Crop Improvement, April 16-22, CO, 1990.
Gelvin, In: *Transgenic Plants*, Kung and Wu (Eds.), Academic Press, San Diego, 49-87, 1993.
Hayashimoto, *Plant Physiol.*, 93:857-863, 1990.
Haymes et al., In: *Nucleic Acid Hybridization, A Practical Approach*, IRL Press, Washington, D.C., 1985
Herman et al., *J. Biol. Chem.*, 280(26):24759-24767, 2005.
Hooykaas and Beijersbergen, *Ann. Rev. Phytopathol.*, 32:157-179, 1994.
Howard and Citovsky, *Bioassays*, 12:103-108, 1990.
Jefferson et al., *Biochem. Soc. Trans.*, 15:7-19, 1987.
Kado, *Crit. Rev. Plant Sci.*, 10:1-32, 1991.
Kanehisa, *Nucl. Acids Res.*, 12:203-213, 1984.
Klee et al., *Ann. Rev. Plant Phys.*, 38:467-486, 1987.
Lessl and Lanka, *Cell*, 77:321-324, 1994.
Pearson and Lipman, *Proc. Natl. Acad. Sci. USA*, 85(8): 2444-2448, 1988.
Ream; *Ann. Rev. Phytopathol.*, 27: 583-618, 1989.
Rogers et al., *Methods Enzymol.*, 153:253-277, 1987.
Rogers et al., *Plant Mol. Biol.*, 5:69-76, 1985.
Sambrook et al., In: *Molecular cloning: a laboratory manual*, 2$^{nd}$ Ed., Cold Spring Harbor Laboratory Press, Cold Spring Harbor, N.Y., 1989.
Sambrook et al., In: *Molecular cloning: a laboratory manual*, 2$^{nd}$ Ed., Cold Spring Harbor Laboratory Press, Cold Spring Harbor, N.Y., 9.52-9.55, 1989.
Sambrook et al., In: *Molecular cloning: a laboratory manual*, 2$^{nd}$ Ed., Cold Spring Harbor Laboratory Press, Cold Spring Harbor, N.Y., 9.47-9.52, 9.56-9.58, 1989.
Shimamoto et al., *Nature*, 338:274-276, 1989.
Vasil et al., *Bio/Technology*, 10:667-674, 1992.
Vasil et al., *Bio/Technology*, 8:429434, 1990.
Wetmur and Davidson, *J. Mol. Biol.*, 31:349-370, 1968.
Winans, *Microbiol. Rev.*, 56:12-31, 1992.
Wising et al. *Ann. Rev. Genetics*, 22, 421, 1988.
Zambryski, *Ann. Rev. Plant Physiol. Plant Mol. Biol.*, 43: 465-490, 1992.
Zupan and Zambryski, *Ann. Rev. Phytopathol.*, 27:583-618, 1995.

What is claimed is:

1. A DNA construct for transforming plants comprising:
   i) at least one T-DNA border region;
   ii) at least one heterologous transgene adjacent to the border region, wherein the heterologous transgene when expressed in a transformed plant provides an agronomic phenotype to the transformed plant;
   iii) a coding region for a bacterial selectable marker; and
   iv) at least one segment of DNA, comprising a cis and/or trans element of a repABC replication origin for maintaining a low copy number of the DNA construct in a bacterium competent for the transformation of at least a first plant cell,
   wherein the at least one segment of DNA comprises replication origin genes repA, repB and repC from *Agrobacterium rhizogenes*, and wherein said segment of DNA comprises a sequence having at least 90% identity to SEQ ID NO:1 or SEQ ID NO:2.

2. The DNA construct according to claim 1, wherein the at least one T-DNA border region is either a right border region or a left border region.

3. The DNA construct according to claim 1, wherein the coding region for the bacterial selectable marker comprises an antibiotic resistance gene selected from the group consisting of a kanamycin resistance gene, gentamycin resistance gene, chloramphenicol resistance gene, spectinomycin resistance gene, streptomycin resistance gene, tetracycline resistance gene, ampicillin resistance gene, blasticidin resistance gene, hygromycin resistance gene, puromycin resistance gene, and Zeocin resistance gene.

4. The DNA construct according to claim 1, wherein the at least one segment of DNA comprises a sequence having at least 90% identity to one or more of SEQ ID NO:32, SEQ ID NO:33, SEQ ID NO:34, SEQ ID NO:35 or SEQ ID NO:36.

5. The DNA construct according to claim 1, wherein the at least one segment of DNA comprises intergenic sequence 1 (igs1) and intergenic sequence 2 (igs2).

6. The DNA construct according to claim 1, wherein the at least one segment of DNA comprises a 16 base pair palindromic sequence.

7. The DNA construct according to claim 1, wherein the bacterium is selected from the group consisting of *Agrobacterium* spp., *Rhizobium* spp., *Sinorhizobium* spp., *Mesorhizobium* spp., *Phyllobacterium* spp., *Ochrobactrum* spp. and *Bradyrhizobium* spp.

8. The DNA construct according to claim 1, further comprising at least a first replication origin for maintaining copies of the construct in *E. coli*.

9. The DNA construct according to claim 8, wherein the replication origin is derived from pBR322 and/or pUC.

10. A cell transformed with the DNA construct of claim 1.

11. The cell of claim 10, defined as a plant cell.

12. The cell of claim 10, defined as a bacterial cell.

13. The bacterial cell of claim 12, wherein the cell is competent for the transformation of at least a first plant cell.

14. The bacterial cell of claim 13, wherein the bacteria is selected from the group consisting of *Agrobacterium* spp., *Rhizobium* spp., *Sinorhizobium* spp., *Mesorhizobium* spp., *Phyllobacterium* spp., *Ochrobactrum* spp. and *Bradyrhizobium* spp.

15. A method for transforming a plant cell comprising: contacting at least a first plant cell with the bacterial cell of claim 13, wherein the bacterial cell is competent for the transformation of said first plant cell; and selecting said first cell based on the presence of at least one heterologous transgene introduced into the plant cell by the bacterial cell.

16. The method of claim 15, wherein the plant cell is a soybean, canola, corn, or cotton plant cell.

17. The method of claim 15, further comprising regenerating a plant from the plant cell.

18. A method of producing food, feed or an industrial product comprising: obtaining a plant produced by the method of claim 17 or a part thereof; and preparing the food, feed or industrial product from the plant or part thereof.

19. The DNA construct according to claim 1, wherein the at least one segment of DNA comprises a sequence having at least 90% identity to SEQ ID NO:3.

* * * * *